(12) United States Patent
Shibutani et al.

(10) Patent No.: US 6,245,779 B1
(45) Date of Patent: Jun. 12, 2001

(54) NAPHTHYRIDINE DERIVATIVES

(75) Inventors: Tadao Shibutani; Yasuo Shoji; Takashi Okamura; Tsuneo Yasuda, all of Naruto; Takeshi Iwamoto, Komatsushima, all of (JP)

(73) Assignee: Otsuka Pharmaceutical Factory, Inc., Naruto (JP)

( * ) Notice: Subject to any disclaimer, the term of this patent is extended or adjusted under 35 U.S.C. 154(b) by 0 days.

(21) Appl. No.: 09/445,564

(22) PCT Filed: Jul. 7, 1998

(86) PCT No.: PCT/JP98/03045
§ 371 Date: Dec. 9, 1999
§ 102(e) Date: Dec. 9, 1999

(87) PCT Pub. No.: WO99/02527
PCT Pub. Date: Jan. 21, 1999

(30) Foreign Application Priority Data

Jul. 10, 1997 (JP) .................................................... 9-185489

(51) Int. Cl.$^7$ .................. A61K 31/4375; A61K 31/541; C07D 471/04; C07D 279/12; A61P 29/00
(52) U.S. Cl. ........................ 514/300; 514/228.2; 544/61; 546/122
(58) Field of Search ............................ 546/122; 514/300, 514/228.2; 544/61

(56) References Cited

U.S. PATENT DOCUMENTS 4,775,686 * 10/1988 Blythin .................................. 514/300

FOREIGN PATENT DOCUMENTS 7-304775  11/1995  (JP) .

OTHER PUBLICATIONS

International Search Report.

* cited by examiner

Primary Examiner—Evelyn Mei Huang

(57) ABSTRACT

The present invention provides a naphthyridine derivative represented by the formula (1)

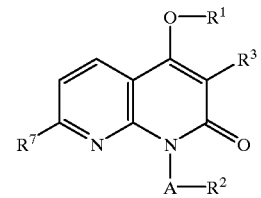

wherein A is lower alkylene; $R^1$ is H or an electron pair "-"; $R^2$ is optionally substituted phenyl;
when $R^1$ is an electron pair "-", $R^3$ is a group represented by

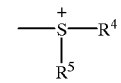

(wherein $R^4$ and $R^5$ each represent lower alkyl, etc.); when $R^1$ is H, $R^3$ is a group —S—$R^6$ (wherein $R^6$ is lower alkyl, etc.); and $R^7$ is H or lower alkyl; and also provides an analgesic composition containing the above derivative as an active ingredient.

18 Claims, No Drawings

NAPHTHYRIDINE DERIVATIVES

This application is the national phase of PCT/JP98/03045 filed on Jul. 7, 1998.

FIELD OF THE INVENTION

The present invention relates to novel naphthyridine derivatives.

BACKGROUND ART

Our research group focused on compounds having a naphthyridine skeleton and continued intensive research thereon to develop compounds having excellent pharmacological effects. As a result, we found novel compounds having anti-inflammatory activity, anti allergic activity, immune regulating activity, analgesic activity and the like (Japanese Unexamined Patent Publication No. 304775/1995).

The novel compounds have potent anti-inflammatory effects but their alagesic effects are not completely satisfactory.

An object of the invention is to provide novel naphthyridine derivatives having potent analgesic effects.

We synthesized compounds in which the substituents at 1-position of the naphthyridine ring varied and carried out pharmacological screening of the same. Consequently we found a group of novel compounds having highly potent analgesic activity as compared with conventional compounds, and accomplished the present invention.

DISCLOSURE OF THE INVENTION

The present invention provides a naphthyridine derivative represented by the formula (1)

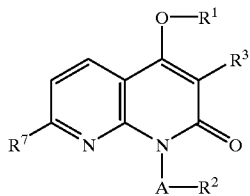

wherein A represents lower alkylene;

$R^1$ represents hydrogen or an electron pair "-";

$R^2$ represents pyridyl; naphthyl; biphenylyl; or phenyl optionally having 1 to 3 substituents selected from the group consisting of halogen, lower alkyl, lower alkoxy and halogen-substituted lower alkoxy;

when $R^1$ is an electron pair "-", $R^3$ represents a group

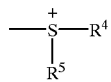

(wherein $R^4$ and $R^5$ are the same or different and each represent lower alkyl, oxoalkyl, phenyl-lower alkyl, hydroxy-lower alkyl, di(lower alkyl)phosphono-lower alkyl, N-lower alkyl-carbamoyl-lower alkyl, lower alkoxycarbonyl-lower alkyl, cycloalkyl, lower alkanoyloxy-lower alkyl, N-lower alkanoylamino-lower alkyl, lower alkoxy-lower alkyl, benzoyloxy-lower alkyl optionally having 1 to 3 substituents selected from the group consisting of lower alkoxy and lower alkanoyloxy on the benzene ring, N,N-di(lower alkyl)carbamoyloxy-lower alkyl, benzyloxy-lower alkyl having 1 to 3 lower alkoxy groups on the benzene ring, N-benzoylamino-lower alkyl having 1 to 3 lower alkoxy groups on the benzene ring, N-phenylcarbamoyl-lower alkyl having 1 to 3 lower alkoxy groups on the benzene ring, diphenylacetoxy-lower alkyl, or phenyl optionally having 1 to 3 substituents selected from the group consisting of lower alkyl, hydroxyl, halogen and lower alkoxy; or $R^4$ and $R^5$ taken together form a heterocyclic ring containing the sulfur atom to which they are attached, wherein the heterocyclic ring may be substituted by 2-furoyl, tri(lower alkoxy)benzoyl or oxo or by phenyl and hydroxyl);

when $R^1$ is hydrogen, $R^3$ is a group —S—$R^6$ (wherein $R^6$ is lower alkyl, oxcalkyl, phenyl-lower alkyl, hydroxy-lower alkyl, di(lower alkyl)phosphono-lower alkyl, N-lower alkylcarbamoyl-lower alkyl, lower alkoxycarbonyl-lower alkyl, cycloalkyl, lower alkanoyloxy-lower alkyl, N-lower alkanoylamino-lower alkyl, lower alkoxy-lower alkyl, benzoyloxy-lower alkyl optionally having 1 to 3 substituents selected from the group consisting of lower alkoxy and lower alkanoyloxy on the benzene ring, N,N-di(lower alkyl) carbamoyloxy-lower alkyl, benzyloxy-lower alkyl having 1 to 3 lower alkoxy groups on the benzene ring, N-benzoylamino-lower alkyl having 1 to 3 lower alkoxy groups on the benzene ring, N-phenylcarbamoyl-lower alkyl having 1 to 3 lower alkoxy groups on the benzene ring, diphenylacetoxy-lower alkyl, or phenyl optionally having 1 to 3 substituents selected from the group consisting of lower alkyl, hydroxyl, halogen and lower alkoxy); and $R^7$ is hydrogen or lower alkyl.

The present invention also provides pharmaceutical compositions containing the above naphthyridine derivative and a pharmaceutically acceptable carrier.

Further, the present invention provides use of the above napthyridine derivative for relieving a patient's pain or use of the above naphthyridine derivative for preparing an analgesic composition.

The present invention also provides a method for relieving a pain in a patient in need of such pain relief, which comprises administering to the patient an effective amount of the naphthyridine derivative defined in claim 1.

The present invention will be described below in detail.

Examples of the groups in the formula (1) are shown below.

The lower alkylene group includes straight- or branched-chain alkylene groups having 1 to 6 carbon atoms, such as methylene, ethylene, ethylidene, trimethylene, tetramethylene, pentamethylene, hexamethylene and the like.

The pyridyl group includes 2-pyridyl, 3-pyridyl and 4-pyridyl.

The naphthyl group includes 1-naphthyl and 2-naphthyl.

The biphenylyl group includes 2-biphenylyl, 3-biphenylyl and 4-biphenylyl.

The halogen atom includes fluorine, chlorine, bromine and iodine.

The lower alkyl group includes straight- or branched-chain alkyl groups having 1 to 6 carbon atoms, such as methyl, ethyl, propyl, isopropyl, butyl, isobutyl, tert-butyl, pentyl, hexyl and the like.

The lower alkoxy group includes straight- or branched-chain alkoxy groups having 1 to 6 carbon atoms, such as methoxy, ethoxy, propoxy, isopropoxy, butoxy, pentyloxy, hexyloxy and the like.

The halogen-substituted lower alkoxy group includes perhalogeno-($C_{1-6}$ alkoxy) groups having as substituents halogen atoms selected from the group consisting of fluorine, chlorine, bromine and iodine, particularly perfluoro-($C_{1-6}$ alkoxy) groups. Specific examples are trifluoromethoxy, pentafluoroethoxy, heptafluoropropoxy, nonafluorobutoxy, undecafluoropentyloxy, tridecafluorohexyloxy and the like.

The phenyl group optionally having 1 to 3 substituents selected from the group consisting of halogen, lower alkyl, lower alkoxy and halogen-substituted lower alkoxy includes phenyl groups optionally having 1 to 3 substituents selected from the group consisting of halogen, $C_{1-6}$ alkyl, $C_{1-6}$ alkoxy and the above perhalogeno-($C_{1-6}$ alkoxy) Specific examples are phenyl, 4-chlorophenyl, 3-chlorophenyl, 2-chlorophenyl, 4-fluorophenyl, 4-bromophenyl, 4-iodophenyl, 2,4-dichlorophenyl, 3,4-dichlorophenyl, 3,5-dichlorcphenyl, 2,4,6-trichlorophenyl, 2,4-dibromophenyl, 4-methoxyphenyl, 3-methoxyphenyl, 2-methoxyphenyl, 4-ethoxyphenyl, 4-propoxyphenyl, 4-isopropoxyphenyl, 4-butoxyphenyl, 4-pentyloxyphenyl, 4-hexyloxyphenyl, 2,4-dimethoxyphenyl, 3,4-dimethoxyphenyl, 3,5-dimethoxyphenyl, 3,4,5-trimethoxyphenyl, 2-chloro-4-methoxyphenyl, 4-chloro-2-methoxyphenyl, 3,5-dichloro-4-methoxyphenyl, 4-methylphenyl, 3-methylphenyl, 2-methylphenyl, 4-ethylphenyl, 4-propylphenyl, 4-isopropylphenyl, 4-n-butylphenyl, 4-t-butylphenyl, 4-n-pentylphenyl, 4-n-hexylphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2,3,4-trimethylphenyl, 2,3,5-trimethylphenyl, 2,4,5-trimethylphenyl, 2,4,6-trimethylphenyl, 3,4,5-trimethylphenyl, 4-trifluoromethoxyphenyl, 3-trifluoromethoxyphenyl, 2-trifluoromethoxyphenyl, 4-pentafluoroethoxyphenyl, 4-heptafluoropropoxyphenyl, 4-nonafluorobutoxyphenyl, 4-undecafluoropentyloxyphenyl, 4-tridecafluorohexyloxyphenyl, 2,3-bis(trifluoromethoxy) phenyl, 2,4-bis(trifluoromethoxy)phenyl, 2,5-bis (trifluoromethoxy)phenyl, 2,6-bis(trifluoromethoxy)phenyl, 3,4-bis(trifluoromethoxy)phenyl, 3,5-bis(trifluoromethoxy) phenyl, 2,3,4-tris(trifluoromethoxy)phenyl, 2,3,5-tris (trifluoromethoxy)phenyl, 2,4,5-tris(trifluoromethoxy) phenyl, 2,4,6-tris(trifluoromethoxy)phenyl, 3,4,5-tris (trifluoromethoxy)phenyl, 4-methoxy-3,5-dimethyphenyl, 4-trifluoromethoxy-3,5-dimethylphenyl, 3-chloro-4-methylphenyl, 3-chloro- 4-trifluoromethoxyphenyl, 3,5-dimethoxy-4-trifluoromethoxyphenyl and the like.

The oxoalkyl group includes oxoalkyl groups having 3 to 8 carbon atoms, such as 2-oxopropyl, 2-oxobutyl, 3-oxobutyl, 2-oxopentyl, 3-oxopentyl, 4-oxopentyl, 5-oxohexyl, 6-oxoheptyl, 7-oxooctyl and the like.

The phenyl-lower alkyl group includes phenyl-$C_{1-6}$ alkyl groups, such as benzyl, 1-phenylethyl, 2-phenylethyl, 3-phenylpropyl, 4-phenylbutyl, 5-phenylpentyl, 6-phenylhexyl and the like.

The hydroxy-lower alkyl group includes hydroxy-$C_{1-6}$ alkyl groups, such as hydroxymethyl, 1-hydroxyethyl, 2-hydroxyethyl, 3-hydroxypropyl, 4-hydroxybutyl, 5-hydroxypentyl, 6-hydroxyhexyl and the like.

The di(lower alkyl)phosphono-lower alkyl group includes di($CC_{1-6}$ alkyl)phosphono-$CC_{1-6}$ alkyl groups, such as dimethylphosphonomethyl, diethylphosphonomethyl, dipropylphosphonomethyl, diisopropylphosphonomethyl, dibutylphosphonomethyl, dipentylphosphonomethyl, dihexylphosphonomethyl, 2-(dimethylphosphono)ethyl, 2-(diethylphphohono)ethyl, 3-(diethylphosphono)propyl, 4-(diethylphosphono)butyl, 5-(diethylphosphono)pentyl, 6-(diethylphosphono)hexyl and the like.

The N-lower alkylcarbamoyl-lower alkyl group includes N-$C_{1-6}$ alkylcarbamoyl-$C_{1-6}$ alkyl groups, such as N-methylcarbamoylmethyl, N-ethylcarbamoylmethyl, N-propylcarbamoylmethyl, N-butylcarbamoylmethyl, N-pentylcarbamoylmethyl, N-hexylcarbamoylmethyl, 2-(N-methylcarbamoyl)ethyl, 3-(N-methylcarbamoyl)propyl, 4-(N-methylcarbamoyl)butyl, 5-(N-methylcarbamoyl) pentyl, 6-(N-methylcarbamoyl)hexyl and the like.

The lower alkoxycarbonyl-lower alkyl group includes $CC_{1-6}$ alkoxycarbonyl-$C_{1-6}$ alkyl groups, such as methoxycarbonylmethyl, ethoxycarbonylmethyl, propoxycarbonylmethyl, butoxycarbonylmethyl, pentyloxycarbonylmethyl, hexyloxycarbonylmethyl, 2-(methoxycarbonyl)ethyl, 3-(methoxycarbonyl)propyl, 4-(methoxycarbonyl)butyl, 5-(methoxycarbonyl)pentyl, 6-(methoxycarbonyl)hexyl and the like.

The cycloalkyl group includes cycloalkyl groups having 3 to 8 carbon atoms, such as cyclopropyl, cyclobutyl, cyclopentyl, cyclohexyl, cycloheptyl, cyclooctyl and the like.

The lower alkanoyloxy-lower alkyl group includes acetoxymethyl, 2-acetoxyethyl, 3-acetoxypropyl, 4-acetoxybutyl, 5-acetoxypentyl, 6-acetoxyhexyl, propionyloxymethyl, butyryloxymethyl, valeryloxymethyl, hexanoyloxymethyl, heptanoyloxymethyl and the like.

The N-lower alkanoylamino-lower alkyl group includes N-acetylaminomethyl, N-propionylaminomethyl, N-butyrylaminomethyl, N-valerylaminomethyl, N-hexanoylaminomethyl, N-heptanoylaminomethyl, 2-(N-acetylamino)ethyl, 3-(N-acetylamino)propyl, 4-(N-acetylamino)butyl, 5-(N-acetylamino)pentyl, 6-(N-acetylamino)hexyl and the like.

The lower alkoxy-lower alkyl group includes methoxymethyl, ethoxymethyl, propoxymethyl, butoxymethyl, pentyloxymethyl, hexyloxymethyl, 2-methoxyethyl, 3-methoxypropyl, 4-methoxybutyl, 5-methoxypentyl, 6-methoxyhexyl and the like.

The benzoyloxy-lower alkyl group optionally having 1 to 3 substituents selected from the group consisting of lower alkoxy and lower alkanoyloxy on the benzene ring includes benzoyloxymethyl, 2-benzoyloxyethyl, 3-benzoyloxypropyl, 4-benzoyloxybutyl, 5-benzoyloxypentyl, 6-benzoyloxyhexyl, 2-methoxybenzoyloxymethyl, 2-ethoxybenzoyloxymethyl, 2-propoxybenzoyloxymethyl, 2-butoxybenzoyloxymethyl, 2-pentyloxybenzoyloxymethyl, 2-hexyloxybenzoyloxymethyl, 2-(2-methoxybenzoyloxy) ethyl, 3-(2-methoxybenzoyloxy)propyl, 4-(2-methoxybenzoyloxy)butyl, 5-(2-methoxybenzoyloxy) pentyl, 6-(2-methoxybenzoyloxy)hexyl, 3,4-dimethoxybenzoyloxymethyl, 2,4-dimethoxybenzoyloxymethyl, 3,5-dimethoxybenzoyloxymethyl, 2-(3,4-dimethoxybenzoyloxy)ethyl, 3-(3, 4-dimethoxybenzoyloxy) propyl, 4-(3,4-dimethoxybenzoyloxy)butyl, 5-(3,4-dimethoxybenzoyloxy)pentyl, 6-(3,4-dimethoxybenzoyloxy)hexyl, 3,4,5-Lrimethoxybenzoyloxymethyl, 2,4,5-trimethoxybenzoyloxymethyl, 2,4,6-trimethoxybenzoyloxymethyl, 2-(3,4,5-trimethoxybenzoyloxy)ethyl, 3-(3,4,5-trimethoxybenzoyloxy)propyl, 4-(3,4,5-trimethoxybenzoyloxy)butyl, 5-(3,4,5- trimethoxybenzoyloxy)pentyl, 6-(3,4,5-trimethoxybenzoyloxy)hexyl, 2-(3,4,5-triethoxybenzoyloxy)ethyl, 2-acetoxybenzoyloxymethyl, 2-propionyloxybenzoyloxymethyl, 2-butyryloxybenzoyloxymethyl, 2-valeryloxybenzoyloxymethyl, 2-hexanoyloxybenzyloxymethyl, 2-heptanoyloxybenzyloxymethyl, 2-(2-acetoxybenzoyloxy)ethyl, 3-(2-acetoxybenzoyloxy)propyl, 4-(2-acetoxybenzoyloxy)butyl, 5-(2-acetoxybenzoyloxy)pentyl, 6-(2-acetoxybenzoyloxy)hexyl, 2,4-diacetoxybenzoyloxymethyl, 3,5-diacetoxybenzoyloxymethyl, 3,4,5-triacetoxybenzoyloxymethyl, 2,4,6-triacetoxybenzoyloxymethyl and the like.

The N,N-di(lower alkyl)carbamoyloxy-lower alkyl group includes N,N-dimethylcarbamoyloxymethyl, N,N-diethylcarbamoyloxymethyl, N,N-dipropylcarbamoyloxymethyl, N,N-dibutylcarbamoyloxymethyl, N,N-dipentylcarbamoyloxymethyl, N,N-dihexylcarbamoyloxymethyl, 2-(N,N-dimethylcarbamoyloxy)ethyl, 3-(N,N-dimethylcarbamoyloxy)propyl, 4-(N,N-dimethylcarbamoyloxy)butyl, 5-(N,N-dimethylcarbamoyloxy)pentyl, 6-(N,N-dimethylcarbamoyloxy)hexyl and the like.

The benzyloxy-lower alkyl group having 1 to 3 lower alkoxy groups on the benzene ring includes 2-methoxybenzyloxymethyl, 2-ethoxybenzyloxymethyl, 2-propoxybenzyloxymethyl, 2-butoxybenzyloxymethyl, 2-pentyloxybenzyloxymethyl, 2-hexyloxybenzyloxymethyl, 2-(2-methoxybenzyloxy)ethyl, 3-(2-methoxybenzyloxy)propyl, 4-(2-methoxybenzyloxy)butyl, 5-(2-methoxybenzyloxy)pentyl, 6-(2-methoxybenzyloxy)hexyl, 3,4-dimethoxybenzyloxymethyl, 2,4-dimethoxybenzyloxymethyl, 3,5-dimethoxybenzyloxymethyl, 2-(3,4-dimethoxybenzyloxy)ethyl, 3-(3,4-dimethoxybenzyloxy)propyl, 4-(3,4-dimethoxybenzyloxy)butyl, 5-(3,4-dimethoxybenzyloxy)pentyl, 6-(3,4-dimethoxybenzyloxy)hexyl, 3,4,5-trimethoxybenzyloxymethyl, 2,4,5-trimethoxybenzyloxymethyl, 2,4,6-trimethoxybenzyloxymethyl, 2-(3,4,5-trimethoxybenzyloxy)ethyl, 3-(3,4,5-trimethoxybenzyloxy)propyl, 4-(3,4,5-trimethoxybenzyloxy)butyl, 5(3,4,5-trimethoxybenzyloxy)pentyl, 6-(3,4,5-trimethoxybenzyloxy)hexyl, 2-(3,4,5-triethoxybenzyloxy)ethyl and the like.

The N-benzoylamino-lower alkyl group having 1 to 3 lower alkoxy groups on the benzene ring includes N-(2-methoxybenzoyl)aminomethyl, N-(2-ethoxybenzoyl)aminomethyl, N-(2-propoxybenzoyl)aminomethyl, N-(2-buthoxybenzoyl)aminomethyl, N-(2-pentyloxybenzoyl)aminomethyl, N-(2-hexyloxybenzoyl)aminomethyl, 2-[N-(2-methoxybenzoyl)amino]ethyl, 3-[N-(2-methoxybenzoyl)amino]propyl, 4-[N-(2-methoxybenzoyl)amino]butyl, 5-[N-(2-methoxybenzoyl)amino]pentyl, 6-[N-(2-methoxybenzoyl)amino]hexyl, N-(3,4-dimethoxybenzoyl)aminomethyl, N-(2,4-dimethoxybenzoyl)aminomethyl, N-(3,5-dimethoxybenzoyl)aminomethyl, 2-[N-(3,4-dimethoxybenzoyl)amino]ethyl, 3-[N-(3,4-dimethoxybenzoyl)amino]propyl, 4-[N-(3,4-dimethoxybenzoyl)amino]butyl, 5-[N-(3,4-dimethoxybenzoyl)amino]pentyl, 6-[N-(3,4-dimethoxybenzoyl)amino]hexyl, N-(3,4,5-trimethoxybenzoyl)aminomethyl, N-(2,4,5-trimethoxybenzoyl)aminomethyl, N-(2,4,6-trimethoxybenzoyl)aminomethyl, 2-[N-(3,4,5-trimethoxybenzoyl)amino]ethyl, 3-[N-(3,4,5-trimethoxybenzoyl)amino]propyl, 4-[N-(3,4,5-trimethoxybenzoyl)amino]butyl, 5-[N-(3,4,5-trimethoxybenzoyl)amino]pentyl, 6-[N-(3,4,5-trimethoxybenzoyl)amino]hexyl, 2-[N-(3,4,5-triethoxybenzoyl)amino]ethyl and the like.

The N-phenylcarbamoyl-lower alkyl group having 1 to 3 lower alkoxy groups on the benzene ring includes N-(2-methoxyphenyl)carbamoylmethyl, N-(2-ethoxyphenyl)carbamoylmethyl, N-(2-propoxyphenyl)carbamoylmethyl, N-(2-butoxyphenyl)carbamoylmethyl, N-(2-pentyloxyphenyl)carbamoylmethyl, N-(2-hexyloxyphenyl)carbamoylmethyl, 2-[N-(2-methoxyphenyl)carbamoyl]ethyl, 3-[N-(2-methoxyphenyl)carbamoyl]propyl, 4-[N-(2-methoxyphenyl)carbamoyl]butyl, 5-[N-(2-methoxyphenyl)carbamoyl]pentyl, 6-[N-(2-methoxyphenyl)carbamoyl]hexyl, N-(3,4-dimethoxyphenyl)carbamoylmethyl, N-(2,4-dimethoxyphenyl)carbamoylmethyl, N-(3,5-dimethoxyphenyl)carbamoylmethyl, 2-[N-(3,4-dimethoxyphenyl)carbamoyl]ethyl, 3-[N-(3,4-dimethoxyphenyl)carbamoyl]propyl, 4-[N-(3,4-dimethoxyphenyl)carbamoyl]butyl, 5-[N-(3,4-dimethoxyphenyl)carbamoyl]pentyl, 6-[N-(3,4-dimethoxyphenyl)carbamoyl]hexyl, N-(3,4,5-trimethoxyphenyl)carbamoylmethyl, N-(2,4,5-trimethoxyphenyl)carbamoylmethyl, N-(2,4,6-trimethoxyphenyl)carbamoylmethyl, 2-[N-(3,4,5-trimethoxyphenyl)carbamoyl]ethyl, 3-[N-(3,4,5-trimethoxyphenyl)carbamoyl]propyl, 4-[N-(3,4,5-trimethoxyphenyl)carbamoyl]butyl, 5-[N-(3,4,5-trimethoxyphenyl)carbamoyl]pentyl, 6-[N-(3,4,5-trimethoxyphenyl)carbamoyl]hexyl, 2-[N-(3,4,5-triethoxyphenyl)carbamoyl]ethyl and the like.

The diphenylacetoxy-lower alkyl group includes diphenylacetoxymethyl, 2-(diphenylacetoxy)ethyl, 3-(diphenylacetoxy)propyl, 4-(diphenylacetoxy)butyl, 5-(diphenylacetoxy)pentyl, 6-(diphenylacetoxy)hexyl and the like.

The phenyl group optionally having 1 to 3 substituents selected from the group consisting of lower alkyl, hydroxyl, halogen and lower alkoxy includes phenyl groups optionally having 1 to 3 substituents selected from the group consisting of $C_{1-6}$ alkyl, hydroxyl, halogen and $C_{1-6}$ alkoxy. Specific examples are phenyl, 4-methylphenyl, 3-methylphenyl, 2-methylphenyl, 4-ethylphenyl, 4-propylphenyl, 4-isopropylphenyl, 4-butylphenyl, 4-tert-butylphenyl, 4-pentylphenyl, 4-hexylphenyl, 2,4-dimethylphenyl, 3,4-dimethylphenyl, 3,5-dimethylphenyl, 3,4,5-trimethylphenyl, 2,4,6-trimethylphenyl, 4-hydroxyphenyl, 3-hydroxyphenyl, 2-hydroxphenyl, 2,4-dihydroxphenyl, 3,4-dihydroxyphenyl, 3,5-dihydroxphenyl, 3,4,5-trihydroxyphenyl, 4-chlorophenyl, 3-chlorophenyl, 2-chlorophenyl, 4-fluorohpenyl, 4-bromophenyl, 4-iodophenyl, 2,4-dichlorophenyl, 3,4-dichlorophenyl, 3,5-dichlorophenyl, 2,4,6-trichlorophenyl, 2,4-dibromophenyl, 4-methoxyphenyl, 3-methoxyphenyl, 2-methoxypehnyl, 4-ethoxyphenyl, 4-propoxyphenyl, 4-isopropoxyphenyl, 4-butoxyphenyl, 4-pentyloxyphenyl, 4-hexyloxyphenyl, 2,4-dimethoxyphenyl, 3,4-dimethoxyphenyl, 3,5-dimethoxyphenyl, 3,4,5-trimethoxyphenyl, 2-hydroxy-4-methylphenyl, 4-hydroxy-2-methylphenyl, 4-hydroxy-3-methylphenyl, 4-hydroxy-3,5-dimethylphenyl, 4-hydroxy-3,5-di-tert-butylphenyl, 2-chloro-4-methylphenyl, 4-chloro-2-methylphenyl, 4-chloro-3-methylphenyl, 4-chloro-3,5-dimethylphenyl, 3,5-dichloro-4-methylphenyl, 2-methoxy- 4-methylphenyl, 4-methoxy-2-methylphenyl, 4-methoxy-3-methylphenyl, 4-methoxy-3,5-dimethylphenyl, 4-methoxy-3,5-di-tert-butylphenyl, 4-chloro-2-hydroxyphenyl, 2-chloro-4-hydroxyphenyl, 3-chloro-4-hydroxyphenyl, 3,5-dichloro-4-hydroxyphenyl, 2-hydroxy-4-methoxyphenyl, 4-hydroxy-2-methoxyphenyl, 4-hydroxy-3-methoxyphenyl, 4-hydroxy-3,5-dimethoxyphenyl, 3,5-dihydroxy-4-methoxyphenyl, 4-chloro-2-methoxyphenyl, 2-chloro-4-methoxyphenyl, 3-chloro-4-methoxyphenyl, 3,5-dichloro-4-methoxyphenyl, 2-chloro-5-hydroxy-4-methoxyphenyl, 2-chloro-5-hydroxy-4-methylphenyl, 2-chloro-4-methoxy-5-methylphenyl, 5-hydroxy-4-methoxy-2-methylphenyl and the like.

The sulfur atom-containing heterocyclic ring which may be optionally substituted with 2-furoyl, tri(lower alkoxy) benzoyl or oxo or with phenyl and hydroxyl includes 5- to 6-membered heterocyclic rings which may be substituted with one substituent selected from 2-furoyl, tri($C_{1-2}$ alkoxy) benzoyl or oxo or with one phenyl group and one hydroxyl group and which may contain, in addition to the sulfur atom to which $R_4$ and $R_5$ are attached, 1 to 2 nitrogen atoms (preferably 1 nitrogen atom) and/or 1 to 2 oxygen atoms (preferably 1 oxygen atom) as hetero atom(s), such as tetrahydrothiophene, tetrahydrothiopyran, 1,4-oxathiane, 1,4-thiazane, 3-oxotetrahydrothiophene, 3-oxotetrahydrothiopyran, 4-oxotetrahydrothiopyran, 4-hydroxy-4-phenyltetrahydrothiopyran, 4-(2-furoyl)-1,4-thiazane, 4-(3,4,5-trimethoxybenzoyl)-1,4-thiazane, 4-(2,4,5-trimethoxybenzoyl)-1,4-thiazane, 4-(3,4,5-triethoxybenzoyl)-1,4-thiazane and the like.

Of the naphthyridine derivatives of the invention, the following compounds are preferable:

(1) A naphthyridine derivative of the formula (1) wherein $R^1$ is an electron pair "-", $R^4$ is lower alkyl, phenyl or hydroxy-lower alkyl, or $R^4$ and $R^5$, taken together with the sulfur atom to which they are attached, form a heterocyclic ring which may be substituted with 2-furoyl, tri(lower alkoxy) benzoyl or oxo.
(2) A naphthyridine derivative of the formula (1) wherein $R^1$ is hydrogen and $R^6$ is lower alkyl or phenyl.
(3) A naphthyridine derivative of the formula (1) wherein A is methylene, $R^1$ is an electron pair "-", $R^4$ is lower alkyl, phenyl or hydroxy-lower alkyl, or $R^4$ and $R^5$, taken together with the sulfur atom to which they are attached, form a heterocyclic ring which may be substituted with 2-furoyl, tri(lower alkoxy)benzoyl or oxo.
(4) A naphthyridine derivative of the formula (1) wherein A is methylene, $R^1$ is an electron pair "-", $R^4$ is lower alkyl, $R^5$ is lower alkyl, oxoalkyl, or phenyl having 1 to 3 members selected from lower alkyl or halogen as the substituent(s), or $R^4$ and $R^5$, taken together with the sulfur atom to which they are attached, form a 1,4-oxathiane ring.
(5) A naphthyridine derivative of the formula (1) wherein A is methylene, $R^1$ is an electron pair "-" and $R^4$ and $R^5$ each represent lower alkyl.
(6) 1-Benzyl-3-(methyl-n-propylsulfonium)-1,8-naphthyridin-2(1H)-on-4-olate or 1-(3,4,5-trimethoxybenzyl)-3-(methyl-n-propylsulfonium)-1,8-naphthyridin-2(1H)-on-4-olate.
(7) A naphthyridine derivative of the formula (1) wherein A is methylene.
(8) A naphthyridine derivative of the formula (1) wherein A is methylene and $R^1$ is an electron pair "-".
(9) A naphthyridine derivative of the formula (1) wherein A is methylene, $R^1$ is an electron pair "-", and $R^2$ is pyridyl, or phenyl optionally having 1 to 3 substituents selected from the group consisting of halogen, lower alkyl and lower alkoxy.
(10) A naphthyridine derivative of the formula (1) wherein A is methylene, $R^1$ is an electron pair "-", $R^2$ is pyridyl; or phenyl optionally having 1 to 3 substituents selected from the group consisting of halogen, lower alkyl and lower alkoxy, $R^4$ is lower alkyl, $R^5$ is lower alkyl, oxoalkyl, lower alkanoyloxy-lower alkyl, benzoyloxy-lower alkyl having 3 lower alkoxy groups as substituents on the benzene ring, phenyl having one substituent selected from lower alkyl and halogen, or $R^4$ and $R^5$, taken together with the sulfur atom to which they are attached, form a 1,4-oxathiane ring.
(11) A naphthyridine derivative of the formula (1) wherein A is methylene, $R^1$ is an electron pair "-", $R^2$ is phenyl optionally having 1 halogen atom or 1 to 3 lower alkoxy groups as substituent(s), and $R^4$ and $R^5$ each represent lower alkyl.
(12) 1-(3,4,5-trimethoxybenzyl)-3-(methyl-n-propylsulfonium)-1,8-naphthyridin-2(1H)-on-4-olate.
(13) A naphthyridine derivative of the formula (1) wherein A represents lower alkylene.

$R^1$ is hydrogen or an electron pair "-", $R^2$ is phenyl optionally having 1 to 3 substituents selected from the group consisting of halogen and lower alkoxy, when $R^1$ is an electron pair "-", $R^3$ is a group represented by

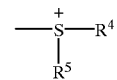

(wherein $R^4$ and $R^5$ are the same or different and each represent lower alkyl, oxoalkyl, phenyl-lower alkyl, hydroxy-lower alkyl, di(lower alkyl)phosphono-lower alkyl, N-lower alkylcarbamoyl-lower alkyl, lower alkoxycarbonyl-lower alkyl, or phenyl optionally having 1 to 3 substituents selected from the group consisting of lower alkyl, hydroxyl, halogen and lower alkoxy, or $R^4$ and $R^5$ taken together form a heterocyclic ring which contains the sulfur atom to which they are attached, wherein the heterocyclic ring may be substituted with 2-furoyl, tri(lower alkoxy)benzoyl or oxo), when $R^1$ is hydrogen, $R^3$ is a group —S—$R^6$ (wherein $R^6$ is lower alkyl, oxoalkyl, phenyl-lower alkyl, hydroxyl-lower alkyl, di(lower alkyl)phosphono-lower alkyl, N-lower alkylcarbamoyl-lower alkyl, lower alkoxycarbonyl-lower alkyl, or phenyl optionally having 1 to 3 substituents selected from the group consisting of lower alkyl, hydroxyl, halogen and lower alkoxy), and $R^7$ is hydrogen;

(14) A naphthyridine derivative of the formula (1) wherein $R^1$ is an electron pair "-", $R^2$ is phenyl optionally having 1 to 3 substituents selected from the group consisting of halogen and lower alkoxy, $R^4$ is lower alkyl, phenyl or hydroxy-lower alkyl, or $R^4$ and $R^5$, taken together with the sulfur atom to which they are attached, form a heterocyclic ring which is optionally substituted with 2-furoyl, tri(lower alkoxy)benzoyl or oxo, and $R^7$ is hydrogen.
(15) A naphthyridine derivative of the formula (1) wherein $R^1$ is hydrogen, $R^2$ is phenyl optionally having 1 to 3 substituents selected from the group consisting of halogen and lower alkoxy, $R^6$ is lower alkyl or phenyl, and $R^7$ is hydrogen.
(16) A naphthyridine derivative of the formula (1) wherein A is methylene, $R^1$ is an electron pair "-", $R^2$ is phenyl optionally having 1 to 3 substituents selected from the group consisting of halogen and lower alkoxy, $R^4$ is lower alkyl, phenyl or hydroxy-lower alkyl, or $R^4$ and $R^5$, taken together with the sulfur atom to which they are attached, form a heterocyclic ring which is optionally substituted with 2-furoyl, tri(lower alkoxy)benzoyl or oxo as a substituent, and $R^7$ is hydrogen.

(17) A naphthyridine derivative of the formula (1) wherein A is methylene and $R^1$ is an electron pair "-", $R^2$ is phenyl optionally having 1 to 3 substituents selected from the group consisting of halogen and lower alkoxy, $R^4$ is lower alkyl, $R^5$ is lower alkyl, oxoalkyl; or phenyl having 1 to 3 members selected from lower alkyl or halogen as the substituent(s), or $R^4$ and $R^5$, taken together with the sulfur atom to which they are attached, form a 1,4-oxathiane ring, and $R^7$ is hydrogen.

(18) A naphthyridine derivative of the formula (1) wherein A is methylene, $R^1$ is an electron pair "-", $R^2$ is phenyl optionally having 1 to 3 substituents selected from the group consisting of halogen and lower alkoxy, $R^4$ and $R^5$ each represent lower alkyl, and $R^7$ is hydrogen.

(20) 1-Benzyl-3-(methyl-n-propylsulfonium)-1,8-naphthyridin-2(1H)-on-4-olate, 1-benzyl-7-methyl-3-(methyl-n-propylsulfonium)-1,8-naphthyridin-2(1H)-on-4-olate or 1-(3,4,5-trimethoxybenzyl)-3-(methyl-n-propylsulfonium)-1,8-naphthyridin-2(1H)-on-4-olate.

The naphthyridine derivatives of the invention can be produced by various processes. Exemplary processes are shown below with reference to reaction schemes.

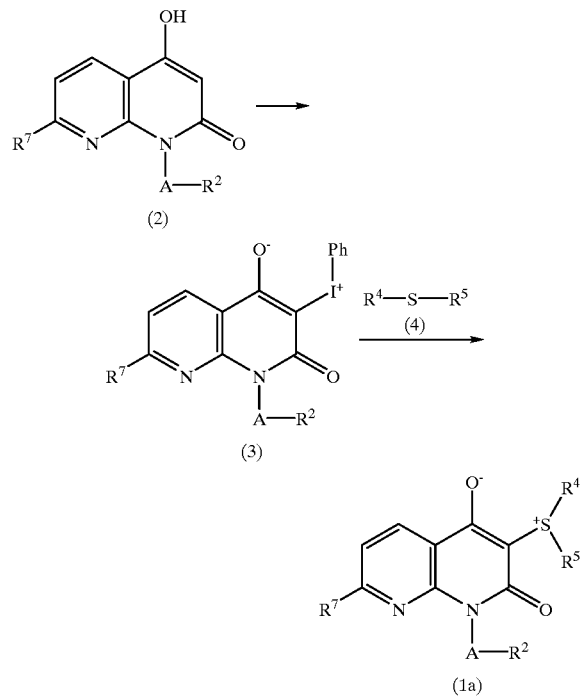

wherein $R^2$, $R^4$, $R^5$, $R^7$ and A are as defined above.

In Reaction Scheme-1, compound (2) is reacted with iodobenzene diacetate in the presence of an alkali to produce compound (3). In the reaction, water is suitable for use as a solvent. Useful alkali includes, for example, sodium carbonate, potassium carbonate, sodium hydrogen carbonate and potassium hydrogen carbonate. The alkali and iodobenzene diacetate are used preferably in an equimolar to slight excess amount, respectively, relative to the starting compound. The reaction is carried out at a temperature of 0° C. to about room temperature and completed in about 1 to 10 hours.

Subsequently, the resulting compound (3) is reacted with thioether derivative (4) to produce compound (1a) of the invention. The reaction may be carried out using a lower alcohol such as methanol, ethanol, trifluoroethanol or the like as a solvent and adding a suitable amount of an acid catalyst such as p-toluenesulfonic acid, acetic acid or the like. Thioether derivative (4) is used preferably in an amount of about 1 to about 10 moles per mole of compound (3). The acid catalyst is used preferably in an amount of 0.005 to 0.5 mole per mole of compound (3). The reaction is carried out at a temperature ranging from room temperature to reflux temperature and completed in about 10 minutes to about 24 hours.

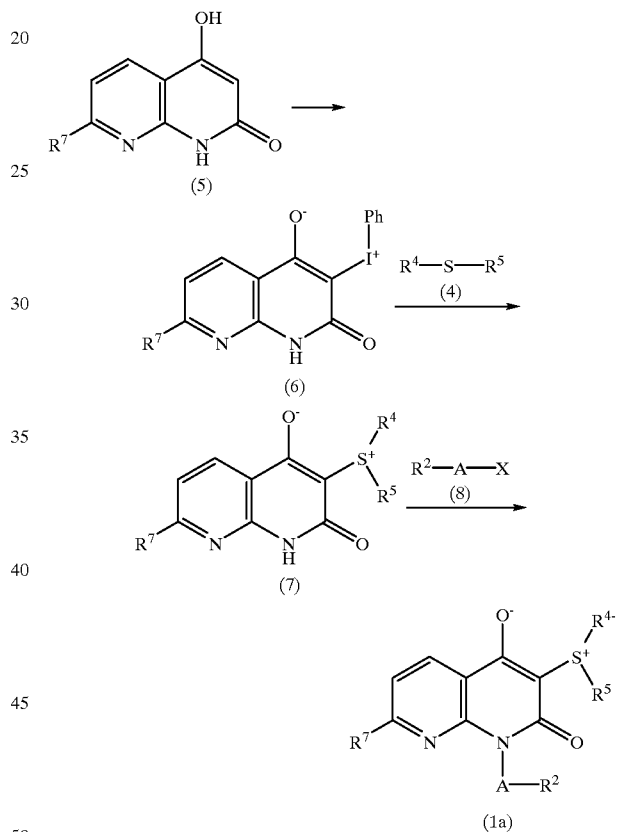

wherein $R^2$, $R^4$, $R^5$, $R^7$ and A are as defined above and X is a halogen atom.

In Reaction Scheme-2, the reaction to convert compound (5) to compound (7) is carried out in a manner similar to the reaction to convert compound (2) to compound (3) in Reaction Scheme-1.

Compound (7) is then reacted with an equimolar to slight excess amount of compound (8) to convert to compound (1a) of the invention. The reaction can be carried out in an inert solvent such as N,N-dimethylformamide (DMF), N,N-dimethylacetamide (DMA) or the like in the presence of a deacidification agent. As the deacidification agent, alkali metal hydrides such as sodium hydride and potassium hydride, and sodium ethoxide are preferably used. These compounds are used preferably in an amount of 1 to 1.5 equivalents relative to compound (7). The reaction is usually carried out at 0° C. to room temperature and completed in 20 minutes to 5 hours.

The resulting compound (1) of the invention is considered to have resonance structures as shown below, and therefore represented by any one of the following structural formulas.

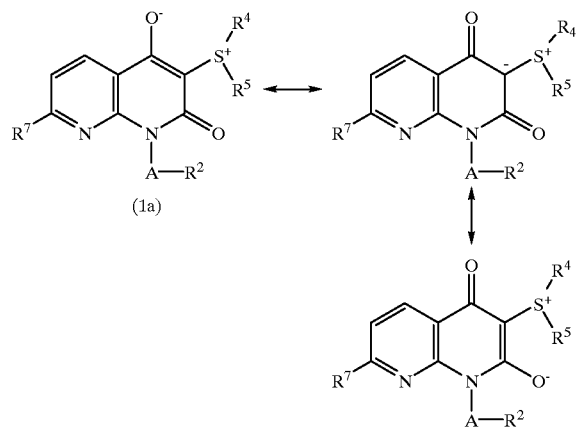

Further, the naphthyridine derivatives of the invention may also be produced by the following process.

[Reaction Scheme-3]

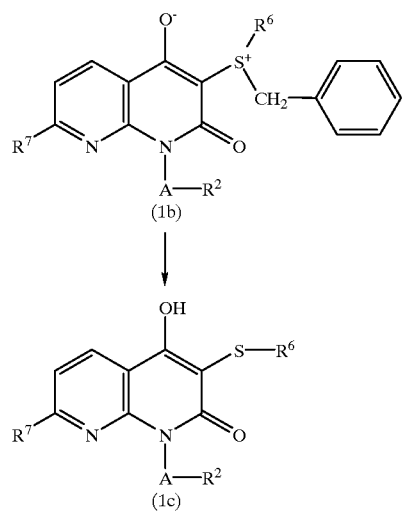

wherein $R^2$, $R^6$, $R^7$ and A are as defined above.

Compound (1b) corresponds to the foregoing compound (1a) wherein $R^4=R^6$ and $R^5$ is benzyl. Thus the compound (1b) can be obtained according to Reaction Scheme-1 or Reaction Scheme-2.

As shown in Reaction Scheme-3, compound (1b) of the invention is treated with an acid catalyst such as p-toluenesulfonic acid, benzenesulfonic acid or the like in an inert solvent such as methanol, ethanol or ethylene glycol to thereby convert it to compound(1c) of the invention. The acid catalyst is used in an amount of 0.005 to 0.5 mole per mole of the compound (1b). The reaction is usually carried out at room temperature to reflux temperature and completed in 30 minutes to 5 hours.

The compounds of the invention obtained according to the aforementioned Reaction Schemes can be easily isolated and purified by conventional separation and purification methods. Useful methods include various methods such as adsorption chromatography, preparative thin-layer chromatography, recrystallization and solvent extraction.

Some of the compounds of the invention exist as optical isomers having sulfur and/or carbon as an asymmetric center. The present invention includes both racemate and optically active isomers. The optically active isomers can be isolated by conventional methods, such as a method using a known optical resolving agent.

The compound of the formula (1) of the invention has excellent analgesic effects and is useful as medicine, particularly as an analgesic. Therefore, the present invention provides a pharmaceutical composition, particularly an analgesic composition.

The pharmaceutical composition of the invention comprises a compound of the formula (1) as an active ingredient together with a suitable pharmaceutically acceptable non-toxic carrier, and is used in the form of a usual pharmaceutical preparation.

Examples of pharmaceutically acceptable carriers for use in the pharmaceutical compositions of the invention are conventional diluents or excipients such as fillers, extenders, binders, humectants, disintegrators, surfactants, lubricants and the like, which are selected and used according to the desired unit dosage forms.

A suitable unit dosage form can be selected from a variety of forms according to the therapeutic purpose. Typical examples are tablets, pills, powders, solutions, suspensions, emulsions, granules, capsules, suppositories, injections (solutions, suspensions, etc.), ointments and the like.

For preparing tablets by molding, usable as the above pharmaceutically acceptable carriers are excipients such as lactose, sucrose, sodium chloride, glucose, urea, starch, calcium carbonate, kaolin, crystalline cellulose, silicic acid and potassium phosphate; binders such as water, ethanol, propanol, simple syrup, glucose syrup, starch solution, gelatin solution, carboxymethyl cellulose, hydroxypropyl cellulose, methyl cellulose and polyvinyl pyrrolidone; disintegrators such as sodium carboxymethyl cellulose, calcium carboxymethyl cellulose, low-substituted hydroxypropyl cellulose, dry starch, sodium alginate, agar powder, naminaran powder, sodium hydrogen-carbonate and calcium carbonate; surfactants such as polyoxyethylene sorbitan fatty acid esters, sodium lauryl sulfate and stearic acid monoglyceride; disintegration inhibitors such as sucrose, stearin, cacao butter and hydrogenated oil; absorption promoters such as quaternary ammonium base and sodium lauryl sulfate; humectants such as glycerin and starch; adsorbents such as starch, lactose, kaolin, bentonite and colloidal silicic acid; and lubricants such as purified talc, stearic acid salt, boric acid powder and polyethylene glycol. If necessary, the tablets can be made into coated tablets, such as sugar-coated tablets, gelatin-coated tablets, enteric tablets, film-coated tablets, double-layered tablets or multiple-layered tablets.

For preparing pills by molding, usable as pharmaceutically acceptable carriers are excipients such as glucose, lactose, starch, cacao butter, hydrogenated vegetable oil, kaolin and talc; binders such as gum arabic powder, tragacanth powder, gelatin and ethanol; and disintegrators such as laminaran and agar.

For formulating suppositories, usable as pharmaceutically acceptable carriers are polyethylene glycol, cacao butter, a higher alcohol or its esters, gelatin, semisynthetic glycerides and the like.

The capsules are usually manufactured in a conventional manner by blending the compound of the invention with one or more pharmaceutically acceptable carriers as exemplified above and encapsulating the mixture into hard gelatin capsule shells, soft capsule shells, etc.

When the compound of the invention is to be provided in an injectable form such as a solution, an emulstion or a suspension, the preparation is preferably sterilized and rendered isotonic to the blood. Diluents for use in such preparation include, for example, water, ethanol, macrogols, propylene glycol, ethoxylated isostearyl alcohol, polyoxyisostearyl alcohol, polyoxyethylene sorbitan fatty acid esters and the like. In this case, sodium chloride, glucose or glycerin may be added to the pharmaceutical composition in an amount sufficient to provide an isotonic solution. Conventional solubilizers, buffers, anesthetics etc. may also be added.

For preparing ointments in the form of pastes, creams, gels, etc., usable as diluent are white petrolatum, paraffin, glycerin, cellulose derivatives, polyethylene glycol, silicone, bentonite and the like.

Furthermore, if desired, coloring agents, preservatives, aromatics, flavors, sweeteners or other medicines may be incorporated into the pharmaceutical composition of the invention to thereby prepare a pharmaceutical preparation.

The proportion of the compound of the invention (active ingredient compound) in the above pharmaceutical composition is not critical and can be selected from a broad range. It is generally preferable that the compound account for about 0.5 to about 90 wt. %, preferably about 1 to about 85 wt. %, of the pharmaceutical composition.

There is no limitation on the methods for administering the pharmaceutical compositions of the invention. Thus, a proper method can be selected according to the dosage form, patient's age, sex and other conditions, severity of disease, etc. For example, the tablets, pills, solutions, suspensions, emulsions, granules and capsules are administered by the oral route. The injections are administered singly or in admixture with glucose, amino acid or like conventional infusions by the intravenous route or by the intramuscular, intradermal, subcutaneous or intraperitoneal route. The suppositories are administered intrarectally.

The dosage of the pharmaceutical preparation is suitably selected according to the intended use, patient's age, sex and other conditions, severity of disease, etc., but may be such that the dosage of the compound of the invention as the active ingredient is preferably about 0.5–20 mg, preferably 1 to 10 mg, per kg body weight a day, for human adult. The pharmaceutical preparation may be administered once a day or in 2–4 divided doses a day.

BEST MODE FOR CARRYING OUT THE INVENTION

In order to describe the present invention in more detail, preparation of the derivatives of the invention will be shown in Examples.

In Examples, Me=methyl, Et=ethyl, n-Pr=n-propyl, n-Bu=n-butyl, Ph=phenyl, and Bn=benzyl.

EXAMPLE 1

Preparation of 1-benzyl-3-(n-butylmethylsulfonium)-1,8-naphthyridin-2(1H)-on-4-olate (1) 3.1 g of sodium carbonate was dissolved in 200 ml of water. Then dissolved in the aqueous solution was 7.0 g of 1-benzyl-4-hydroxy-1,8-naphthyridin-2(1H)-one. Further 9.0 g of iodobenzene diacetate was added at room temperature, followed by stirring at room temperature for 5 hours.

After completion of the reaction, the crystals precipitated were collected by filtration, washed sequentially with water, methanol and diethyl ether and dried under reduced pressure at room temperature for 20 hours to give 10.1 g of 1-benzyl-3-(phenyliodonium)-1,8-naphthyridin-2(1H)-on-4-olate as crystals.

mp: 147–149° C. (decomposition); $^1$H-NMR ($\delta$:ppm) (measured in DMSO-$d_6$ solvent); 5.56(2H, s), 7.11–7.26 (6H, m), 7.33–7.54(3H, m), 7.84(2H, d, J=7.4), 8.32(1H, d, J=7.4), 8.50(1H, d, J=4.5).

(2) 2.2 g of the crystals obtained above, 0.55 g of n-butylmethylsulfide and 100 mg of p-toluenesulfonic acid were dissolved in 20 ml of trifluoroethanol and the solution was stirred at room temperature for 30 minutes. After completion of the reaction, the trifluoroethanol was distilled off under reduced pressure, and the residue was purified by silica gel column chromatography (eluent; methanol:chloroform=1:20). The crystals obtained were washed with diethyl ether-n-hexane to provide 1.53 g of the title compound.

Table 1 shows the structure and physical properties of the compound obtained. $^1$H-NMR measurement was performed using DMSO-$d_6$ as a solvent and tetramethylsilane (TMS) as an internal standard.

EXAMPLES 2–29

The compounds shown in Table 1 were prepared following the procedure of Example 1.

EXAMPLE 30

Preparation of 1-(2-chlorobenzyl)-3-(methyl-n-propylsulfonium)-1,8-naphthyridin-2(1H)-on-4-olate First, following the reaction of Example 1 and using 4-hydroxy-1,8-naphthyridin-2(1H)-one, there was prepared 3-(phenyliodonium)-1,8-naphthylidin-2(1H)-on-4-olate, which was then converted to 3-(methyl-n-propylsulfonium)-1,8-naphthylidin-2(1H)-on-4-olate.

Stated more specifically,
(1) 3.5 g of sodium carbonate was dissolved in 200 ml of water. Then dissolved in this aqueous solution was 5.1 g of 4-hydroxy-1,8-naphthyridin-2(1H)-one. Further 10.1 g of iodobenzene diacetate was added thereto at room temperature, followed by stirring at room temperature for 2 hours.

After completion of the reaction, the crystals precipitated were collected by filtration, washed sequentially with water, methanol and diethyl ether and dried under reduced pressure at room temperature for 20 hours to give 10.6 g of 3-(phenyliodonium)-1,8-naphthyridin-2(1H)-on-4-olate as crystals.

mp: 268–271° C. (decomposition).

(2) 10.6 g of the crystals obtained above, 3.1 g of methyl-n-propylsulfide and 200 mg of p-toluenesulfonic acid were dissolved in 50 ml of trifluoroethanol, and the solution was stirred at 50° C. for 30 minutes. After completion of the reaction, trifluoroethanol was distilled off under reduced pressure, and the residue was purified by silica gel column chromatography (eluent; methanol:chloroform=1:10). The crystals obtained were washed with diethyl ether-n-hexane to provide 6.9 g of 3-(methyl-n-propylsulfonium)-1,8-naphthyridin-2(1H)-on-4-olate as crystals.

mp: 172–174° C. $^1$H-NMR ($\delta$:ppm) (measured in DMSO-$d_6$ solvent); 1.04 (3H, t, J=7.4), 1.51–1.80(2H, m), 3.17(3H, s), 3.29–3.41(1H, m), 3.99–4.09(1H, m), 7.17(1H, dd, J=4.9, 7.9), 8.24(1H, d, J=7.9), 8.51(1H, d, J=4.9), 10.97(1H, brs).

Then 250 mg of 60% sodium hydride was dissolved in 20 ml of DMF and 1.3 g of the crystals obtained above was added to the solution at 0° C., followed by stirring at 0° C. for 10 minutes. Further 1.2 g of 2-chlorobenzylbromide was added, followed by stirring at room temperature for 1 hour. After completion of the reaction, water was added to the reaction mixture. The mixture was extracted with 30 ml of chloroform three times. The chloroform layers were combined, washed with water, dried over anhydrous magnesium sulfate and concentrated under reduced pressure. The residue was purified by silica gel column chromatography (eluent; methanol:chloroform=1:30) and the crystals obtained were washed with diethyl ether-n-hexane to provide 0.77 g of the title compound as crystals. Table 1 shows the structure and physical properties of the compound obtained.

EXAMPLES 31–35

The compounds shown in Table 1 were prepared following the procedure of Example 30.

EXAMPLE 36

Preparation of 1-benzyl-4-hydroxy-3-phenylthio-1,8-naphthyridin-2(1H)-one 2.5 g of the compound obtained in Example 29 and 200 mg of p-toluene sulfonic acid were dissolved in 50 ml of methanol, and the solution was refluxed for 2 hours. After completion of the reaction, the reaction mixture was concentrated under reduced pressure and the crude crystals obtained were washed with diethyl ether to give 1.43 g of the title compound as crystals. Table 1 shows the structure and physical properties of the compound obtained.

EXAMPLES 37–38

The compounds shown in Table 1 were prepared following the procedure of Example 36.

TABLE 1

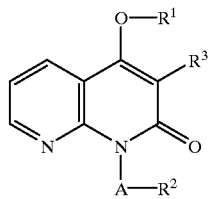

| No. | A | $R^1$ | $R^2$ | $R^3$ | m.p. (° C.) | $^1$H-NMR (δ:ppm) |
|---|---|---|---|---|---|---|
| 1 | —CH$_2$— | — | Ph | Me\|—S$^+$—n-Bu | 140\|142 | 0.84(3H, t, J=7.2), 1.29–1.60 (4H, m), 3.13(3H, s), 3.29–3.40(1H, m), 3.92–4.03(1H, m), 5.48(2H, s), 7.13–7.29 (6H, m), 8.29(1H, d, J=7.6), 8.49(1H, d, J=4.6) |
| 2 | —CH$_2$— | — | Ph | (tetrahydrothiophenium) | 168\|169 | 2.01–2.17(2H, m), 2.60–2.71 (2H, m), 3.43–3.68(4H, m), 5.48(2H, s), 7.17(1H, dd, J= 4.7, 7.7), 7.18–7.29(5H, m), 8.29(1H, d, J=7.7), 8.49(1H, d, J=4.7) |
| 3 | —CH$_2$— | — | Ph | Me\|—S$^+$—C$_2$H$_4$—OH | 163\|164 | 3.11(3H, s), 3.58–3.80(3H m), 3.85–3.97(1H, m), 5.26 (1H, brs), 5.47(2H, s), 7.16 (1H, dd, J=4.7, 7.7), 7.18–7.30(5H, m), 8.29(1H, d, J=7.7), 8.49(1H, d, J=4.7) |
| 4 | —CH$_2$— | — | Ph | Me\|—S$^+$—C$_3$H$_6$—OH | 120\|121 | 1.63–1.78(2H, m), 3.15(3H, s), 3.43–3.55(1H, m), 3.86–4.00(1H, m), 4.73(1H, brs), 5.48(2H, s), 7.16(1H, dd, J= 4.7, 7.7), 7.18–7.28(5H, m), 8.28(1H, d, J=7.7), 8.49(1H, d, J=4.7) |
| 5 | —CH$_2$— | — | Ph | Me\|—S$^+$—C$_6$H$_4$—OH | 193\|195 | 3.57(3H, s), 5.47(2H, s), 6.93(2H, d, J=8.7), 7.11–7.28 (6H, m), 7.75(2H, d, J=8.7), 8.29(1H, d, J=7.7), 8.50(1H, d, J=4.7), 10.36(1H, brs) |

TABLE 1-continued

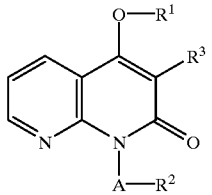

| No. | A | R¹ | R² | R³ | m.p. (°C.) | ¹H-NMR (δ:ppm) |
|---|---|---|---|---|---|---|
| 6 | —CH₂— | — | Ph | Me–S⁺(–)–C₆H₄–Me (para) | 128–129 | 2.35(3H, s), 3.61(3H, s), 5.47(2H, s), 7.18(1H, dd, J=4.7, 7.7), 7.21–7.26(5H, m), 7.39(2H, d, J=8.2), 7.71(2H, d, J=8.2), 8.28(1H, d, J=7.7), 8.51(1H, d, J=4.7) |
| 7 | —CH₂— | — | Ph | Me–S⁺(–)–n-Pr | 129–130 | 0.97(3H, t, J=6.9), 1.43–1.71 (2H, m), 3.13(3H, s), 3.23–3.41(1H, m), 3.90–4.02(1H, m), 5.49(2H, s), 7.12–7.28 (6H, m), 8.28(1H, d, J=7.9), 8.50(1H, d, J=4.9) |
| 8 | —CH₂— | — | Ph | Me–S⁺(–)–Et | 139–140 | 1.18(3H, t, J=7.4), 3.13(3H, s), 3.34–3.49(1H, m), 3.83–3.98(1H, m), 5.48(2H, s), 7.13–7.28(6H, m), 8.28(1H, d, J=7.4), 8.49(1H, d, J=4.5) |
| 9 | —CH₂— | — | Ph | Me–S⁺(–)–CH₂–COOMe | 130–131 | 3.19(3H, s), 3.67(3H, s), 4.80(1H, d, J=15.3), 5.00(1H, d, J=15.3), 5.47(2H, s), 7.12–7.27(6H, m), 8.28(1H, d, J=7.4), 8.50(1H, d, J=4.9) |
| 10 | —CH₂— | — | Ph | Me–S⁺(–)–CH₂–C(=O)–NH–Me | 229–231 | 2.62(2H, d, J=4.5), 3.13(3H, s), 4.58(1H, d, J=14.3), 4.87(1H, d, J=14.3), 7.11–7.28(6H, m), 8.28(1H, d, J=7.4), 8.37(1H, brs), 8.49(1H, d, J=4.7) |
| 11 | —CH₂— | — | Ph | Me–S⁺(–)–CH₂–P(=O)(OEt)(OEt) | 97–98 | 1.08(3H, t, J=6.9), 1.13(3H, t, J=6.9), 3.23(3H, s), 3.91–4.03(4H, m), 4.12(1H, dd, J=13.6, 14.1), 4.77(1H, dd, J=13.6, 14.1), 5.48(2H, s), 7.12–7.29(6H, m), 8.29(1H, d, J=7.7), 8.51(1H, d, J=4.7) |
| 12 | —CH₂— | — | Ph | S⁺(C₂H₄–OH)(C₂H₄–OH) | 150–151 | 3.55–3.83(6H, m), 3.91–4.03(2H, m), 5.24(2H, brs), 5.48(2H, s), 7.10–7.30(6H, m), 8.27(1H, d, J=7.7), 8.49(1H, d, J=4.7) |
| 13 | —CH₂— | — | Ph | Me–S⁺(–)–C₃H₆–C(=O)–Me | 113–114 | 1.60–1.85(2H, m), 2.03(3H, s), 2.59(2H, t, J=6.9), 3.14(3H, s), 3.23–3.40(1H, m), 3.83–3.94(1H, m), 5.48(2H, s), 7.12–7.29(6H, m), 8.27(1H, d, J=7.4), 8.49(1H, d, J=4.9) |
| 14 | —CH₂— | — | Ph | Me–S⁺(–)–C₆H₄–Cl (meta) | 155–156 | 3.66(3H, s), 5.48(2H, s), 7.18(1H, dd, J=4.7, 7.7), 7.19–7.30(5H, m), 7.57–7.75(3H, m), 7.92(1H, s), 8.29(1H, d, J=7.7), 8.53(1H, d, J=4.7) |

TABLE 1-continued

| No. | A | R¹ | R² | R³ | m.p. (° C.) | ¹H-NMR (δ:ppm) |
|---|---|---|---|---|---|---|
| 15 | —CH₂— | — | Ph | (1-thiomorpholinium, S-linked with O in ring) | 201\|202 | 3.21–3.31(2H, m), 3.83–3.99 (2H, m), 4.34–4.45(2H, m), 4.62–4.76(2H, m), 5.56(2H, s), 7.26(1H, dd, J=4.8, 7.6), 7.28–7.39(5H, m), 8.38(1H, d, J=7.6), 8.59(1H, d, J=4.8) |
| 16 | —CH₂— | — | Ph | (dimethylsulfonium-phenyl with OH) | 179\|180 | 3.50(3H, s), 5.50(2H, s), 6.85–7.47(10H, m), 8.31(1H, d, J=7.4), 8.53(1H, d, J=4.9), 11.35(1H, brs) |
| 17 | —CH₂— | — | Ph | (dimethylsulfonium-3,4,5-trimethoxyphenyl) | 176\|177 | 3.64(3H, s), 3.70(3H, s), 3.75(6H, s), 5.51(2H, d, J=7.9), 7.14–7.29(8H, m), 8.32(1H, d, J=7.4), 8.53 (1H, d, J=4.4) |
| 18 | —CH₂— | — | Ph | (methylthiomorpholinium-N-furoyl) | 160\|161 | 3.33–3.41(2H, m), 3.51–3.73(2H, m), 4.45–4.69(2H, m), 4.74–4.86(2H, m), 5.47 (2H, s), 6.68(1H, dd, J=2.0, 3.4), 7.12–7.28(7H, m), 7.91(1H, s), 8.28(1H, d, J=7.9), 8.51(1H, d, J=4.8) |
| 19 | —CH₂— | — | Ph | (methylthiomorpholinium-N-(3,4,5-trimethoxybenzoyl)) | 215\|216 | 3.30–3.71(4H, m), 3.70 (3H, s), 3.79(6H, s), 4.11–4.31(2H, m), 4.43–4.56(2H, m), 5.49(2H, s), 6.80(2H, s), 7.15–7.29(6H, m), 8.31(1H, d, J=7.9), 8.52(1H, d, J=4.5) |
| 20 | —CH₂— | — | Ph | (1-methyl-3-oxotetrahydrothiophenium) | 158\|160 | 2.65–2.80(1H, m), 3.08–3.22(1H, m), 3.40–3.51 (1H, m), 3.77(1H, d, J=17.0), 3.90–4.01(1H, m), 4.07 (1H, d, J=17.0), 5.46(2H, s), 7.17(1H, dd, J=4.6, 7.8), 7.19–7.30(5H, m), 8.27(1H, d, J=7.8), 8.50(1H, d, J=4.6) |
| 21 | —CH₂— | — | Ph | (1-methylthianium) | 180\|182 | 1.30–1.55(1H, m), 1.67–1.90 (3H, m), 2.11–2.28(2H, m), 3.12–3.23(2H, m), 4.40–4.54 (2H, m), 5.47(2H, s), 7.17 (1H, dd, J=4.6, 7.6), 7.20–7.31(5H, m), 8.29(1H, d, J=7.6), 8.50(1H, d, J=4.6) |
| 22 | —CH₂— | — | Ph | (dimethylsulfonium-CH₂-C(O)Me) | 135\|137 | 2.24(3H, s), 3.08(3H, s), 4.94 (1H, d, J=16.8), 5.26(1H, d, J=16.8), 5.47(2H, s), 7.17 (1H, dd, J=4.5, 7.9), 7.21–7.29(5H, m), 8.28(1H, d, J=7.9), 8.50(1H, d, J=4.5) |

TABLE 1-continued

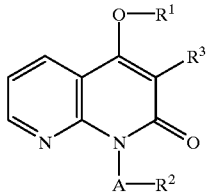

| No. | A | R¹ | R² | R³ | m.p. (° C.) | ¹H-NMR (δ:ppm) |
|---|---|---|---|---|---|---|
| 23 | —CH₂— | — | Ph | Et—S⁺—n-Pr | 119–121 | 0.97(3H, t, J=7.4), 1.20(3H, t, J=7.4), 1.44–1.73(2H, m), 3.23–3.43(1H, m), 3.85–4.03 (1H, m), 5.50(2H, s), 7.15–7.29(6H, m), 8.28(1H, d, J=7.7), 8.49(1H, d, J=4.7) |
| 24 | —CH₂— | — | Ph | n-Pr—S⁺—n-Pr | 124–125 | 0.97(6H, t, J=7.4), 1.41–1.75(4H, m), 3.21–3.35(2H, m), 3.92–4.06(2H, m), 5.49 (2H, s), 7.10–7.30(6H, m), 8.27(1H, d, J=7.7), 8.49 (1H, d, J=4.7) |
| 25 | —CH₂— | — | Ph | Et—S⁺—Et | 154–155 | 1.19(6H, t, J=7.4), 3.31–3.48(2H, m), 3.83–4.01(2H, m), 5.49(2H, s), 7.10–7.30 (6H, m), 8.28(1H, d, J=7.7), 8.50(1H, d, J=4.7) |
| 26 | —CH₂— | — | Ph | n-Bu—S⁺—n-Bu | 129–130 | 0.84(6H, t, J=7.1), 1.29–1.61(4H, m), 3.21–3.40(2H, m), 5.50(2H, s), 7.11–7.29 (6H, m), 8.27(1H, d, J=7.4), 8.49(1H, d, J=4.7) |
| 27 | —CH₂— | — | Ph | Bn—S⁺—n-Pr | 156–158 | 0.98(3H, t, J=7.3), 1.50–1.79 (2H, m), 3.31–3.43(1H, m), 4.06–4.17(1H, m), 4.68(1H, d, J=11.5), 5.33(1H, d, J=11.5), 5.44(2H, d, J=6.1), 7.02–7.37(11H, m), 8.24(1H, d, J=7.6), 8.46(1H, d, J=4.8) |
| 28 | —CH₂— | — | Ph | Me—S⁺—Bn | 149–151 | 3.21(3H, s), 4.69(1H, d, J=11.5), 5.32(1H, d, J=11.5), 5.43(2H, d, J=7.4), 7.05–7.33 (11H, m), 8.25(1H, d, J=7.6), 8.46(1H, d, J=4.8) |
| 29 | —CH₂— | — | Ph | Ph—S⁺—Bn | 157–160 | 5.29(1H, d, J=11.1), 5.46 (2H, d, J=11.1), 5.88(1H, d, J=11.1), 7.05–7.44(12H, m), 7.57–7.68(2H, m), 7.90–8.01 (2H, m), 8.27(1H, d, J=7.7), 8.49(1H, d, J=4.7) |
| 30 | —CH₂— | — | 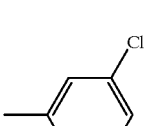 | Me—S⁺—n-Pr | 180–181 | 0.97(3H, t, J=7.4), 1.47–1.75(2H, m), 3.13(3H, s), 3.22–3.41(1H, m), 3.88–4.03 (1H, m), 5.50(2H, s), 6.67(1H, d, J=7.4), 7.10–7.30 (3H, m), 7.47(1H, d, J=7.9), 8.32(1H, d, J=7.7), 8.45(1H, d, J=4.7) |
| 31 | —CH₂— | — | 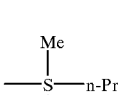 | Me—S⁺—n-Pr | 105–107 | 0.97(3H, t, J=7.4), 1.45–1.70 (2H, m), 3.14(3H, s), 3.21–3.40(1H, m), 3.90–4.02(1H, m), 5.47(2H, s), 7.15–7.33 (5H, m), 8.29(1H, d, J=7.7), 8.50(1H, d, J=4.7) |

TABLE 1-continued

| No. | A | R¹ | R² | R³ | m.p. (° C.) | ¹H-NMR (δ:ppm) |
|---|---|---|---|---|---|---|
| 32 | —CH₂— | — | 4-Cl-C₆H₄— | Me—S⁺—n-Pr | 138–139 | 0.96(3H, t, J=7.4), 1.40–1.70(2H, m), 3.34(3H, s), 3.25–3.41(1H, m), 3.89–4.01(1H, m), 5.45(2H, s), 7.13–7.38(5H, m), 8.27(1H, d, J=7.6), 8.50(1H, d, J=4.7) |
| 33 | —CH₂— | — | 3,4-(OMe)₂-C₆H₃— | Me—S⁺—n-Pr | 110–112 | 0.97(3H, t, J=7.4), 1.42–1.72(2H, m), 3.12(3H, s), 3.20–3.38(1H, m), 3.67(3H, s), 3.93–4.03(1H, m), 5.40(2H, s), 6.70–6.83(2H, m), 6.97(1H, s), 7.16(1H, dd, J=4.7, 7.7), 8.26(1H, d, J=7.7), 8.52(1H, d, J=4.7) |
| 34 | —CH₂— | — | 3,4,5-(OMe)₃-C₆H₂— | Me—S⁺—n-Pr | 136–137 | 1.04(3H, t, J=7.4), 1.52–1.81(2H, m), 3.21(3H, s), 3.30–3.51(1H, m), 3.67(3H, s), 3.74(6H, s), 4.05–4.15(1H, m), 5.49(2H, s), 6.65(2H, s), 7.24(1H, dd, J=4.7, 7.7), 8.35(1H, d, J=7.7), 8.60(1H, d, J=4.7) |
| 35 | —C₂H₄— | — | Ph | Me—S⁺—n-Pr | 100–101 | 1.04(3H, t, J=7.4), 1.47–1.75(2H, m), 2.90–3.01(2H, m), 3.17(3H, s), 3.27–3.47(1H, m), 3.97–4.08(1H, m), 4.48–4.62(2H, m), 7.20–7.41(6H, m), 8.35(1H, d, J=7.7), 8.66(1H, d, J=4.7) |
| 36 | —CH₂— | H | Ph | —S—Ph | 164–166 | 5.61(2H, s), 7.10–7.30(10H, m), 7.36(1H, dd, J=4.9, 7.9), 8.42(1H, d, J=7.9), 8.68(1H, d, J=4.9), 11.71(1H, brs) |
| 37 | —CH₂— | H | Ph | —S—Me | 98–100 | 2.31(3H, s), 5.61(2H, s), 7.15–7.30(5H, m), 7.33(1H, dd, J=4.7, 7.9), 8.34(1H, d, J=7.9), 8.62(1H, d, J=4.7), 11.05(1H, brs) |
| 38 | —CH₂— | H | Ph | —S-n-Pr | 90–92 | 0.92(3H, t, J=6.9), 1.41–1.55(2H, m), 2.79(2H, t, J=6.9), 5.62(2H, s), 7.15–7.25(5H, m), 7.33(1H, dd, J=4.9, 7.9), 8.34(1H, d, J=7.9), 8.62(1H, d, J=4.9), 10.93(1H, brs) |

EXAMPLES 39 TO 100

(1) Preparation of Intermediates

The following compounds were synthesized following the procedure of step (1) of Example 1.

(a) 1-Benzyl-7-methyl-3-(phenyliodonium)-1,8-naphthyridin-2(1H)-on-4-olate mp: 139–140° C.; $^1$H-NMR ($\delta$:ppm) (measured in DMSO-$d_6$ solvent); 2.47 (3H, s), 5.53(2H, s), 7.01(1H, d, J=7.9), 7.10–7.53(8H, m), 7.83(2H, d, J=8.4), 8.20(1H, d, J=7.9).

(b) 1-(1-Phenylethyl)-3-(phenyliodonium)-1,8-naphthyridin-2(1H)-on-4-olate mp: 83–86° C.; $^1$H-NMR ($\delta$:ppm) (measured in DMSO-$d_6$ solvent); 1.89 (3H, d), 6.81–6.90(1H, m), 7.13–7.55(9H, m), 7.79(2H, d, J=7.6), 8.23(1H, d, J=7.6), 8.37–8.48(1H, m).

(c) 1-(4-Methoxybenzyl)-3-(phenyliodonium)-1,8-naphthyridin-2(1H)-on-4-olate mp: 128–130° C.; $^1$H-NMR ($\delta$:ppm) (measured in DMSO-$d_6$ solvent); 3.68(3H, s), 5.48(2H, s), 6.80(2H, d, J=8.9), 7.15(1H, dd, J=4.9, 7.9), 7.22(1H, d, J=8.9), 7.36–7.55(3H, m), 7.84(1H, d, J=7.4), 8.31(1H, d, J=7.9), 8.51(1H, d, J=4.9).

(d) 1-(3,4-Dimethoxybenzyl)-3-(phenyliodonium)-1,8-naphthyridin-2(1H)-on-4-olate mp: 167–170° C.; $^1$H-NMR ($\delta$:ppm) (measured in DMSO-$d_6$ solvent); 3.62(3H, s), 3.67(3H, s), 5.48(2H, s), 6.70–6.81 (2H, m), 6.96 (1H, s), 7.15(1H, dd, J=4.7, 7.7), 7.35–7.43(2H, m), 7.48–7.55(1H, m), 7.85(2H, d, J=7.4), 8.32(1H, d, J=4.7), 8.52(1H, d, J=4.7).

(e) 1-(3,4,5-Trimethoxybenzyl)-3-(phenyliodonium)-1,8-naphthyridin-2(1H)-on-4-olate mp: 132–134° C.; $^1$H-NMR ($\delta$:ppm) (measured in DMSO-$d_6$ solvent); 3.58(3H, s), 3.60(6H, s), 5.48(2H, s), 6.56(2H, s), 7.16(1H, dd, J=4.7, 7.7), 7.35–7.55(3H, m), 7.86(2H, d, J=7.7), 8.33(1H, d, J=7.7), 8.52(1H, d, J=4.7).

(f) 1-(3,4, 5-Trimethoxybenzyl)-7-methyl-3-(phenyliodonium)-1,8-naphthyridin-2(1H)-on-4-olate mp: 125–127° C.; $^1$H-NMR ($\delta$:ppm) (measured in DMSO-$d_6$ solvent); 2.53(3H, s), 3.58(3H, s), 3.63(6H, s), 5.44(2H, s), 6.71(2H, s), 7.02(1H, d, J=7.7), 7.33–7.41(2H, m), 7.45–7.55(1H, m), 7.85(2H, d, J=7.2), 8.19(1H, d, J=7.7).

(g) 1-(2-Phenylethyl)-3-(phenyliodonium)-1,8-naphthyridin-2(1H)-on-4-olate mp: 139–140° C.; $^1$H-NMR ($\delta$:ppm) (measured in DMSO-$d_6$ solvent); 2.83–2.95(2H, m), 4.47–4.61(2H, m), 7.11–7.55(9H, m), 7.84(2H, d, J=7.4), 8.31(1H, d, J=7.9), 8.58(1H, d, J=4.9).

(2) Production of the Desired Compounds

The compounds shown in Table 2 were prepared following the procedure of step (2) of Example 1 and using a suitable intermediate selected from the above compounds (a) to (f) and the compound obtained in step (1) of Example 1.

EXAMPLES 101–116

The compounds shown in Table 2 were prepared following the procedure of Example 30.

TABLE 2
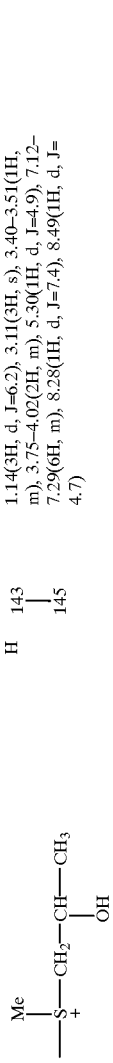
| No. | A | R¹ | R² | R³ | R⁷ | m.p. (° C.) | ¹H-NMR (δ: ppm) |
|---|---|---|---|---|---|---|---|
| 39 | —CH₂— | — | Ph | 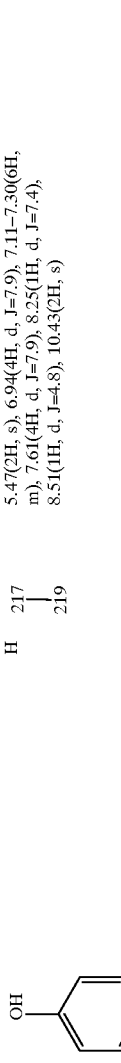 | H | 143–145 | 1.14(3H, d, J=6.2), 3.11(3H, s), 3.40–3.51(1H, m), 3.75–4.02(2H, m), 5.30(1H, d, J=4.9), 7.12–7.29(6H, m), 8.28(1H, d, J=7.4), 8.49(1H, d, J=4.7) |
| 40 | —CH₂— | — | Ph |  | H | 217–219 | 5.47(2H, s), 6.94(4H, d, J=7.9), 7.11–7.30(6H, m), 7.61(4H, d, J=7.9), 8.25(1H, d, J=7.4), 8.51(1H, d, J=4.8), 10.43(2H, s) |
| 41 | —CH₂— | — | Ph | 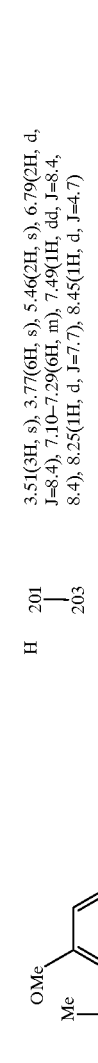 | H | 134–135 | 1.23–2.27(10H, m), 3.22(3H, s), 4.21–4.37(1H, m), 5.55(2H, s), 7.18–7.38(6H, m), 8.35(1H, d, J=7.7), 8.56(1H, d, J=4.7) |
| 42 | —CH₂— | — | Ph | 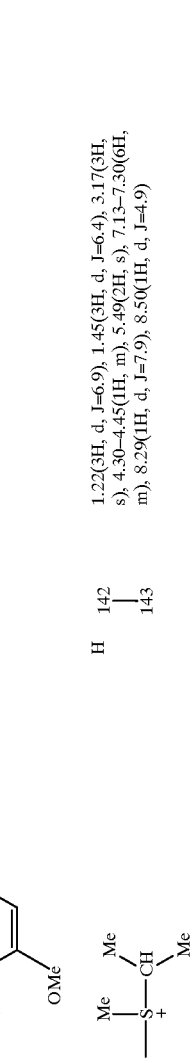 | H | 201–203 | 3.51(3H, s), 3.77(6H, s), 5.46(2H, s), 6.79(2H, d, J=8.4), 7.10–7.29(6H, m), 7.49(1H, dd, J=8.4, 8.4), 8.25(1H, d, J=7.7), 8.45(1H, d, J=4.7) |
| 43 | —CH₂— | — | Ph | Me—CH—S⁺—Me with Me groups | H | 142–143 | 1.22(3H, d, J=6.9), 1.45(3H, d, J=6.4), 3.17(3H, s), 4.30–4.45(1H, m), 5.49(2H, s), 7.13–7.30(6H, m), 8.29(1H, d, J=7.9), 8.50(1H, d, J=4.9) |

TABLE 2-continued

| No. | A | R¹ | R² | R³ | R⁷ | m.p. (° C.) | ¹H-NMR (δ: ppm) |
|---|---|---|---|---|---|---|---|
| 44 | —CH₂— | — | Ph | Me—S⁺—CH₂—CH(Me)Me | H | 157–158 | 0.98(3H, d, J=6.9), 0.99(3H, d, J=6.9), 1.73–1.90 (1H, m), 3.13(3H, s), 3.14–3.20(1H, m), 3.95–4.04 (1H, m), 5.49(2H, s), 7.13–7.29(6H, m), 8.29(1H, d, J=7.9), 8.50(1H, d, J=4.5) |
| 45 | —CH₂— | — | Ph | Me—CH(H)(Me)—S-n-Pr⁺ | H | 127–128 | 0.96(3H, t, J=7.4), 1.22(3H, d, J=7.7), 1.47(3H, d, J=7.7), 1.48–1.75(2H, m), 3.20–3.31(1H, m), 3.97–4.10(1H, m), 4.35–4.49(1H, m), 5.50(2H, s), 7.10–7.35(6H, m), 8.28(1H, d, J=7.7), 8.50(1H, d, J=4.7) |
| 46 | —C₂H₄— | — | Ph | Me—S⁺—CH(Me)Me | H | 46–48 | 1.17(3H, d, J=6.9), 1.44(3H, d, J=6.9), 2.80–2.95 (2H, m), 3.11(3H, s), 4.25–4.40(1H, m), 4.43–4.56 (2H, m), 7.13–7.36(6H, m), 8.27(1H, d, J=7.4), 8.59(1H, d, J=4.9) |
| 47 | —CH₂— | — | Ph | Me—S-n-Pr⁺ | Me | 140–141 | 1.41–1.71(2H, m), 2.46(3H, s), 3.12(3H, s), 3.22–3.37(1H, m), 3.90–4.02(1H, m), 5.46(2H, s), 7.02 (1H, d, J=7.9), 7.13–7.35(5H, m), 8.15(1H, d, J=7.9) |
| 48 | —CH₂— | — | Ph | Me—S-n-Bu⁺ | Me | 117–118 | 0.83(3H, t, J=7.2), 1.30–1.61(4H, m), 2.46(3H, s), 3.12(3H, s), 3.27–3.40(1H, m), 3.92–4.03(1H, m), 5.46(2H, s), 7.02(1H, d, J=7.7), 7.10–7.35(5H, m), 8.15(1H, d, J=7.7) |
| 49 | —CH₂— | — | Ph | Me—S-Et⁺ | Me | 149–151 | 1.16(3H, t, J=7.4), 2.46(3H, s), 3.11(3H, s), 3.30–3.45(1H, m), 3.82–3.97(1H, m), 5.46(2H, s), 7.02 (1H, d, J=7.7), 7.13–7.33(5H, m), 8.15(1H, d, J=7.7) |
| 50 | —CH₂— | — | Ph | Me—S⁺—cyclopentyl | H | 104–106 | 1.55–2.18(8H, m), 3.16(3H, s), 4.62–4.74(1H, m), 5.48(2H, s), 7.12–7.30(6H, m), 8.28(1H, d, J=7.7), 8.49(1H, d, J=4.7) |

TABLE 2-continued
| No. | A | R¹ | R² | R³ | R⁷ | m.p. (° C.) | ¹H-NMR (δ: ppm) |
|---|---|---|---|---|---|---|---|
| 51 | —CH₂— | — | Ph | 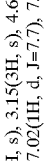 | Me | 138–140 | 1.19(3H, d, J=6.9), 1.44(3H, d, J=6.9), 2.46(3H, s), 3.15(3H, s), 4.27–4.42(1H, m), 5.46(2H, s), 7.02(1H, d, J=7.9), 7.13–7.35(5H, m), 8.15(1H, d, J=7.9) |
| 52 | —CH₂— | — | Ph | 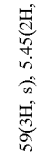 | Me | 142–144 | 1.55–2.18(8H, m), 2.46(3H, s), 3.15(3H, s), 4.60–4.74(1H, m), 5.46(2H, s), 7.02(1H, d, J=7.7), 7.13–7.35(5H, m), 8.15(1H, d, J=7.7) |
| 53 | —CH₂— | — | Ph |  | Me | 139–141 | 2.35(3H, s), 2.47(3H, s), 3.59(3H, s), 5.45(2H, s), 7.03(1H, d, J=7.9), 7.14–7.31(5H, m), 7.38(2H, d, J=8.4), 7.70(2H, d, J=8.4), 8.15(1H, d, J=7.9) |
| 54 | —CH₂— | — |  | | Me | 167–169 | 0.96(3H, t, J=7.4), 1.42–1.70(2H, m), 2.51(3H, s), 3.12(3H, s), 3.21–3.32(1H, m), 3.60(3H, s), 3.69(6H, s), 3.94–4.05(1H, m), 5.38(2H, s), 6.73(2H, s), 7.03(1H, d, J=7.9), 8.13(1H, d, J=7.9) |
| 55 | —CH₂— | — | | | Me | 169–171 | 1.16(3H, t, J=7.4), 2.52(3H, s), 3.11(3H, s), 3.30–3.43(1H, s), 3.60(3H, s), 3.69(6H, s), 3.88–3.98(1H, m), 5.38(2H, s), 6.72(2H, s), 7.03(1H, d, J=7.9), 8.14(1H, d, J=7.9) |

TABLE 2-continued

| No. | A | R¹ | R² | R³ | R⁷ | m.p. (° C.) | ¹H-NMR (δ: ppm) |
|---|---|---|---|---|---|---|---|
| 56 | —CH₂— | — | — | (2,6-dimethoxy-4-methylphenyl with Me, S-n-Bu sulfonium) | Me | 102—104 | 0.82(3H, t, J=7.2), 1.30–1.60(4H, m), 2.52(3H, s), 3.12(3H, s), 3.21–3.33(1H, m), 3.60(3H, s), 3.70 (6H, s), 3.95–4.08(1H, m), 5.38(2H, s), 6.74(2H, s), 7.03(1H, d, J=7.9), 8.14(1H, d, J=7.9) |
| 57 | —CH₂— | — | — | (2,6-dimethoxy-4-methylphenyl with Me, S-Et sulfonium) | H | 147—149 | 1.18(3H, t, J=7.4), 3.14(3H, s), 3.32–3.43(1H, m), 3.60(3H, s), 3.67(6H, s), 3.88–3.99(1H, m), 5.42 (2H, s), 6.58(2H, s), 7.18(1H, dd, J=4.7, 7.7), 8.28 (1H, d, J=7.7), 8.53(1H, d, J=4.7) |
| 58 | —CH₂— | — | — | (2,6-dimethoxy-4-methylphenyl with Me, S-n-Bu sulfonium) | H | 65—67 | 0.83(3H, t, J=7.2), 1.33–1.58(4H, m), 3.13(3H, s), 3.28–3.40(1H, m), 3.59(3H, s), 3.67(6H, s), 3.95–4.08(1H, m), 5.42(2H, s), 6.58(2H, s), 7.18(1H, dd, J=4.7, 7.7), 8.28(1H, d, J=7.7), 8.53(1H, d, J=4.7) |
| 59 | —CH₂— | — | — | (2,6-dimethoxy-4-methylphenyl with Me, S-CH₂-CH(Me)₂ sulfonium) | H | 87—89 | 1.06(3H, d, J=6.9), 1.10(3H, d, J=6.9), 1.80–1.95 (1H, m), 3.11–3.20(1H, s), 3.21(3H, s), 3.68(3H, s), 3.75(6H, s), 4.08–4.17(1H, m), 5.49(2H, s), 6.67(2H, s), 7.25(1H, dd, J=4.5, 7.4), 8.36(1H, d, J=7.4), 8.61(1H, d, J=4.5) |

TABLE 2-continued

[Structure: pyridinone fused with pyridine ring bearing R³, OR¹, N-A-R², and R⁷ substituents]

| No. | A | R¹ | R² | R³ | R⁷ | m.p. (° C.) | ¹H-NMR (δ: ppm) |
|---|---|---|---|---|---|---|---|
| 60 | —CH₂— | — | — | 3,5-dimethyl-4-methoxy with trimethylsulfonium (Me-S⁺(Me)-CH(Me)) on 2,6-dimethoxy-4-methylphenyl | H | 151–153 | 1.22(3H, d, J=7.4), 1.46(3H, d, J=7.4), 3.17(3H, s), 3.59(3H, s), 3.66(6H, s), 4.30–4.43(1H, m), 5.42(2H, s), 6.57(2H, s), 7.18(1H, dd, J=4.7, 7.4), 8.27(1H, d, J=7.4), 8.53(1H, d, J=4.7) |
| 61 | —CH₂— | — | Ph | tetrahydrothiophenium on 2,6-dimethoxy-4-methylphenyl | Me | 163–165 | 1.99–2.12(2H, m), 2.46(3H, s), 2.57–2.71(2H, m), 3.43–3.67(4H, m), 5.45(2H, s), 7.02(1H, s), 7.13–7.34(6H, m), 8.15(1H, d, J=7.7) |
| 62 | —CH₂— | — | — | tetrahydrothiophenium on 2,6-dimethoxy-4-methylphenyl | H | 135–137 | 2.01–2.18(2H, m), 2.55–2.73(2H, m), 3.40–3.57 (4H, m), 3.60(3H, s), 3.66(6H, s), 5.41(2H, s), 6.58(2H, s), 7.18(1H, dd, J=4.7, 7.7), 8.29(1H, d, J=7.7), 8.53(1H, d, J=4.7) |
| 63 | —CH₂— | — | — | cyclopentyl-S⁺(Me)- on 2,6-dimethoxy-4-methylphenyl | H | 133–135 | 1.55–2.21(8H, m), 3.17(3H, s), 3.60(3H, s), 3.67 (6H, m), 4.62–4.73(1H, m), 5.42(2H, s), 6.58(2H, s), 7.18(1H, dd, J=4.7, 7.9), 8.28(1H, d, J=7.9), 8.53(1H, d, J=4.7) |
| 64 | —CH₂— | — | Ph | Me-S⁺(—C₂H₄—O—C(=O)—Me)- on 2,6-dimethoxy-4-methylphenyl | H | 118–120 | 1.90(3H, s), 3.17(3H, s), 3.70–3.82(1H, m), 4.10–4.23(2H, m), 4.27–4.41(1H, m), 5.47(2H, s), 7.13–7.29(6H, m), 8.26(1H, d, J=7.7), 8.49(1H, d, J=4.7) |

TABLE 2-continued

[Structure shown at top of table: pyridinone/naphthyridinone core with substituents R¹O-, R³, =O, N-A-R², and R⁷]

| No. | A | R¹ | R² | R³ | R⁷ | m.p. (° C.) | ¹H-NMR (δ: ppm) |
|---|---|---|---|---|---|---|---|
| 65 | —CH₂— | — | 2,6-(OMe)₂-4-Me-C₆H₂ | Me-S⁺(—C₂H₄—OH)— | H | 92—94 | 3.12(3H, s), 3.59(3H, s), 3.66(6H, s), 3.67–3.81 (3H, m), 3.90–3.99(1H, m), 5.24(1H, brs), 5.41(2H, s), 6.58(2H, s), 7.18(1H, dd, J=4.7, 7.7), 8.27(1H, d, J=7.7), 8.53(1H, d, J=4.7) |
| 66 | —CH₂— | — | 2,6-(OMe)₂-4-Me-C₆H₂ | Me-S⁺(—C₂H₄—O—C(O)—Me)— | H | 117—119 | 1.90(3H, s), 3.17(3H, s), 3.59(3H, s), 3.67(6H, s), 3.69–3.80(1H, m), 4.12–4.40(3H, m), 5.40(2H, s), 6.58(2H, s), 7.18(1H, dd, J=4.7, 7.7), 8.28(1H, d, J=7.7), 8.54(1H, d, J=4.7) |
| 67 | —CH₂— | — | Ph | Me-S⁺(—C₂H₄—OH)— | Me | 170—171 | 2.46(3H, s), 3.35(3H, s), 3.52–3.79(3H, m), 3.85–3.95(1H, m), 5.25(1H, brs), 5.45(2H, s), 7.02(1H, d, J=7.7), 7.13–7.35(5H, m), 8.14(1H, d, J=7.7) |
| 68 | —CH₂— | — | 2,6-(OMe)₂-4-Me-C₆H₂ | Me-S⁺(—C₂H₄—OH)— | Me | 140—142 | 2.51(3H, s), 3.11(3H, s), 3.60(3H, s), 3.69(6H, s), 3.70–4.00(4H, m), 5.24(1H, brs), 5.38(2H, s), 6.73(2H, s), 7.03(1H, d, J=7.9), 8.14(1H, d, J=7.9) |
| 69 | —CH₂— | — | Ph | Me-S⁺(—C₂H₄—O—C(O)—Me)— | Me | 139—140 | 1.90(3H, s), 2.46(3H, s), 3.15(3H, s), 3.69–3.81 (1H, m), 4.10–4.39(3H, m), 5.45(2H, s), 7.03(1H, d, J=7.9), 7.13–7.35(5H, m), 8.14(1H, d, J=7.9) |

TABLE 2-continued

| No. | A | R$^1$ | R$^2$ | R$^3$ | R$^7$ | m.p. (° C.) | $^1$H-NMR (δ: ppm) |
|---|---|---|---|---|---|---|---|
| 70 | —CH$_2$— | — | 3,4,5-tri-OMe-phenyl (methyl-substituted) | Me-S$^+$-C$_2$H$_4$-O-C(O)-Me | Me | 115–117 | 1.89(3H, s), 2.50(3H, s), 3.16(3H, s), 3.60(3H, s), 3.70(6H, s), 3.71–3.80(1H, m), 4.10–4.40(3H, m), 5.37(2H, s), 6.74(2H, s), 7.03(1H, d, J=7.9), 8.14 (1H, d, J=7.9) |
| 71 | —CH$_2$— | — | Ph | Me-S$^+$-C$_3$H$_6$-O-C(O)-Me | H | 138–140 | 1.81–1.93(2H, m), 1.97(3H, s), 3.15(3H, s), 3.33–3.44(1H, m), 3.98–4.12(3H, m), 5.48(2H, s), 7.17 (1H, dd, J=4.8, 7.6), 7.20–7.29(5H, m), 8.28(1H, d, J=7.6), 8.50(1H, d, J=4.8) |
| 72 | —CH$_2$— | — | Ph | Me-S$^+$-C$_2$H$_4$-O-C(O)-Ph | H | 188–190 | 3.21(3H, s), 3.73–3.89(1H, m), 4.45–4.75(3H, m), 5.38(2H, s), 7.09–7.20(6H, m), 7.52–7.61(1H, m), 7.83(2H, d, J=7.6), 8.24(1H, d, J=7.6), 8.47(1H, d, J=4.7) |
| 73 | —CH$_2$— | — | Ph | Me-S$^+$-C$_2$H$_4$-O-C(O)-(3,4,5-tri-OMe-phenyl) | H | 200–202 | 3.19(3H, s), 3.72(3H, s), 3.75(6H, s), 3.76–3.85 (1H, m), 4.30–4.41(1H, m), 4.45–4.55(1H, m), 4.70–4.82(1H, m), 5.34(2H, s), 7.11(1H, dd, J=4.7, 7.6), 7.13–7.23(7H, m), 8.19(1H, d, J=7.6), 8.43(1H, d, J=4.7) |
| 74 | —CH$_2$— | — | Ph | Me-S$^+$-C$_2$H$_4$-OMe | H | 168–169 | 3.13(3H, s), 3.22(3H, s), 3.41–3.53(1H, m), 3.64–3.79(2H, m), 4.02–4.13(1H, m), 5.48(2H, s), 7.16 (1H, dd, J=4.7, 7.7), 7.18–7.25(5H, m), 8.28(1H, d, J=7.7), 8.49(1H, d, J=4.7) |
| 75 | —CH$_2$— | — | Ph | Me-S$^+$-Me | H | 180–182 | 3.13(6H, s), 5.47(2H, s), 7.17(1H, dd, J=4.7, 7.7), 7.20–7.29(5H, m), 8.27(1H, d, J=7.7), 8.49(1H, d, J=4.7) |

TABLE 2-continued

![Structure: pyridone with R3, O-R1, carbonyl, N-A-R2, R7 on pyridine ring fused]

| No. | A | R1 | R2 | R3 | R7 | m.p. (°C.) | 1H-NMR (δ: ppm) |
|---|---|---|---|---|---|---|---|
| 76 | —CH2— | — | Ph | Me—S+—CH2—CH(Me)—O—C(O)—Me | H | 179–180 | 1.27(3H, t, J=6.4), 1.83(3H, s), 3.14(3H, s), 3.53–3.65(1H, m), 4.27–4.37(1H, m), 4.75–4.90(1H, m), 5.47(2H, s), 7.15(1H, dd, J=4.7, 7.7), 7.18–7.30 (5H, m), 8.27(1H, d, J=4.7), 8.49(1H, d, J=4.7) |
| 77 | —CH2— | — | Ph | Me—S+—C2H4—O—C(O)—Et | H | 131–133 | 0.92(3H, t, J=7.4), 2.19(2H, q, J=7.4), 3.17(3H, s), 3.71–3.82(1H, m), 4.17–4.41(3H, m), 5.47(2H, s), 7.17(1H, dd, J=4.5, 7.4), 7.19–7.30(5H, m), 8.27(1H, d, J=7.4), 8.50(1H, d, J=4.5) |
| 78 | —CH2— | — | Ph | Me—S+—C2H4—O—C(O)—n-Pr | H | 83–85 | 0.74(3H, t, J=7.4), 1.38–1.49(2H, m), 2.14(2H, t, J=7.4), 3.17(3H, s), 3.66–3.80(1H, m), 4.15–4.41(3H, m), 5.46(2H, s), 7.17(1H, dd, J=4.9, 7.4), 7.18–7.29(5H, m), 8.27(1H, d, J=7.4), 8.49(1H, d, J=4.9) |
| 79 | —CH2— | — | Ph | Me—S+—C2H4—O—C(O)—N(Me)2 | H | 160–161 | 2.70(6H, s), 3.16(3H, s), 3.67–3.78(1H, m), 4.05–4.15(1H, m), 4.22–4.43(2H, m), 5.47(2H, s), 7.16 (1H, dd, J=4.6, 7.8), 7.18–7.29(5H, m), 8.27(1H, d, J=7.8), 8.49(1H, d, J=4.6) |
| 80 | —CH2— | — | 4-Me-2,OMe(OMe)C6H3 | Me—S+—C2H4—OH | H | 166–168 | 3.12(3H, s), 3.68(6H, s), 3.69–3.98(4H, m), 5.25 (1H, brs), 5.40(2H, s), 6.75(1H, d, J=7.6), 6.80 (1H, d, J=7.6), 6.99(1H, s), 7.16(1H, dd, J=4.9, 7.9), 8.27(1H, d, J=7.9), 8.51(1H, d, J=4.9) |
| 81 | —CH2— | — | 4-Me-2,OMe(OMe)C6H3 | Me—S+—C2H4—O—C(O)—Me | H | 158–159 | 1.91(3H, s), 3.17(3H, s), 3.68(3H, s), 3.69(3H, s), 3.70–3.81(1H, m), 4.11–4.40(3H, m), 5.40(2H, s), 6.74(1H, d, J=8.4), 6.80(1H, d, J=8.4), 6.98(1H, s), 7.17(1H, dd, J=4.9, 7.4), 8.27(1H, d, J=7.4), 8.52(1H, d, J=4.9) |
| 82 | —CH2— | — | Ph | Me—S+—C2H4—N(H)—C(O)—Me | H | 157–159 | 1.80(3H, s), 3.15(3H, s), 3.30–3.41(2H, m), 3.71–3.83(2H, m), 5.47(2H, s), 7.17(1H, dd, J=4.7, 7.7), 7.19–7.30(5H, m), 8.15(1H, brs), 8.27(1H, d, J=7.7), 8.49(1H, d, J=4.7) |

TABLE 2-continued

![structure: R3, O-R1, =O on pyridinone ring fused with pyridine bearing R7, N-A-R2]

| No. | A | R1 | R2 | R3 | R7 | m.p. (°C.) | 1H-NMR (δ: ppm) |
|---|---|---|---|---|---|---|---|
| 83 | —CH2— | — | — | 3,4,5-tri-OMe-phenyl | Me-S+(—C2H4—NHC(O)Me) | H | 170–171 | 1.79(3H, s), 3.15(3H, s), 3.25–3.40(2H, m), 3.59 (3H, s), 3.67(6H, s), 3.68–3.92(2H, m), 5.41(2H, s) 6.59(2H, s), 7.17(1H, dd, J=4.7, 7.7), 8.14(1H, brs), 8.27(1H, d, J=7.7), 8.52(1H, d, J=4.7) |
| 84 | —CH2— | — | Ph | 4-OMe-phenyl | Me-S+(—C2H4—O-C(O)-(2-acetoxy)phenyl) | H | 103–105 | 2.25(3H, s), 3.21(3H, s), 3.73–3.88(1H, m), 4.35–4.50(2H, m), 4.55–4.68(1H, m), 5.40(2H, s), 7.10–7.28(8H, m), 7.59–7.66(1H, m), 7.84(1H, d, J=7.9), 8.25(1H, d, J=7.9), 8.48(1H, d, J=4.9) |
| 85 | —CH2— | — | — | 4-OMe-phenyl | Me-S+(—C2H4—O-C(O)Me) | H | 103–105 | 1.91(3H, s), 3.17(3H, s), 3.69(3H, s), 3.70–3.82 (1H, m), 4.13–4.27(2H, m), 4.30–4.41(1H, m), 5.39 (2H, s), 6.79(2H, d, J=8.6), 7.17(1H, dd, J=4.7, 7.7), 7.22(2H, d, J=8.6), 8.26(1H, d, J=7.7), 8.51 (1H, d, J=4.7) |
| 86 | —CH2— | — | — | 4-OMe-phenyl | Me-S+(—C2H4—OH) | H | 171–172 | 3.11(3H, s), 3.55–3.67(1H, m), 3.69(3H, s), 3.70–3.98(3H, m), 5.25(1H, brs), 5.40(2H, s), 6.79(2H, d, J=8.9), 7.15(1H, dd, J=4.7, 7.7), 7.23(2H, d, J=8.9), 8.26(1H, d, J=7.7), 8.51(1H, d, J=4.7) |
| 87 | —CH2— | — | — | 4-OMe-phenyl | Me-S+(—C2H4—O-C(O)-(3,4,5-tri-OMe)phenyl) | H | 188–190 | 3.27(3H, s), 3.74(3H, s), 3.80(3H, s), 3.84(6H, s), 3.85–3.95(1H, m), 4.35–4.48(1H, m), 4.51–4.64 (1H, m), 4.80–4.90(1H, m), 5.35(2H, s), 6.81(2H, d, J=8.9), 7.19(1H, dd, J=4.7, 7.7), 7.22(2H, d, J=8.9), 7.25(2H, s), 8.27(1H, d, J=7.7), 8.53(1H, d, J=4.7) |

TABLE 2-continued
| No. | A | R¹ | R² | R³ | R⁷ | m.p. (°C.) | ¹H-NMR (δ: ppm) |
|---|---|---|---|---|---|---|---|
| 88 | —CH₂— | — | — | 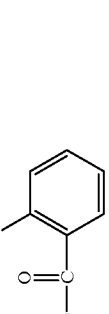 | H | 95–97 | 2.32(3H, s), 3.27(3H, s), 3.73(3H, s), 3.74–3.93 (1H, m), 4.40–4.73(3H, m), 5.39(2H, s), 6.81(2H, d, J=8.2), 7.15–7.30(5H, m), 7.61–7.72(1H, m), 7.90 (1H, d, J=7.9), 8.31(1H, d, J=7.7), 8.57(1H, d, J= 4.7) |
| 89 | —CH₂— | — | — |  | H | 75–77 | 0.92(3H, t, J=7.2), 1.35–1.65(4H, m), 3.21(3H, s), 3.33–3.43(1H, m), 3.77(3H, s), 4.02–4.12(1H, m), 5.49(2H, s), 6.89(2H, d, J=8.7), 7.24(1H, dd, J=4.7 7.7), 7.30(1H, d, J=8.7), 8.35(1H, d, J=7.7), 8.60 (1H, d, J=4.7) |
| 90 | —CH₂— | — | Ph | 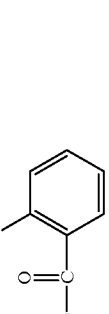 | H | 151–153 | 3.13(3H, s), 3.61(3H, s), 3.74(6H, s), 3.75–3.87 (3H, m), 4.10–4.22(1H, m), 4.35(2H, s), 5.47(2H, s), 6.63(2H, s), 7.11–7.26(6H, m), 8.28(1H, d, J= 7.4), 8.49(1H, d, J=4.5) |
| 91 | —CH₂— | — | — | 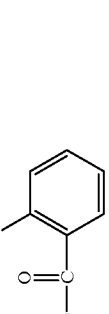 | H | 油状物 | 3.21(3H, s), 3.70(3H, s), 3.74(3H, s), 3.75–3.95 (3H, m), 4.21–4.30(1H, m), 4.43(2H, s), 5.48(2H, s), 6.72(2H, s), 6.83(2H, d, J=8.9), 7.24(1H, dd, J=4.7 7.7), 7.28(2H, d, J=8.9), 8.35(1H, d, J=7.7), 8.59 (1H, d, J=4.7) |

TABLE 2-continued

| No. | A | R$^1$ | R$^2$ | R$^3$ | R$^7$ | m.p. (°C.) | $^1$H-NMR (δ: ppm) |
|---|---|---|---|---|---|---|---|
| 92 | —CH$_2$— | — | Ph | Me-S$^+$(—C$_2$H$_4$—O—C(O)—CH(Ph)$_2$) | H | 131–133 | 3.11(3H, s), 3.73–3.89(1H, m), 4.13–4.22(1H, m), 4.25–4.49(2H, m), 5.11(1H, s), 5.46(2H, s), 7.10–7.35(16H, m), 8.29(1H, d, J=7.7), 8.50(1H, d, J=4.7) |
| 93 | —CH$_2$— | — | 4-MeO-C$_6$H$_4$-CH$_2$ | Me-S$^+$(—C$_3$H$_6$—OH) | H | 123–125 | 1.61–1.77(2H, m), 3.14(3H, s), 3.37–3.51(3H, m), 3.69(3H, s), 3.89–3.99(1H, m), 4.73(1H, brs), 5.40(2H, s), 6.81(2H, d, J=8.9), 7.16(1H, dd, J=4.4, 7.4), 7.22(1H, d, J=8.9), 8.26(1H, d, J=7.4), 8.51(1H, d, J=4.4) |
| 94 | —CH$_2$— | — | 4-MeO-C$_6$H$_4$-CH$_2$ | 1-Me-4-OH-4-Ph-tetrahydrothiopyranium | H | 245–247 | 2.00–2.12(2H, m), 2.35–2.45(2H, m), 2.98–3.09(2H, m), 5.03–5.17(2H, m), 5.49(2H, s), 5.59(1H, brs), 7.13–7.41(9H, m), 7.57(2H, d, J=7.4), 8.31(1H, d, J=7.7), 8.51(1H, d, J=4.7) |
| 95 | —CH$_2$— | — | Ph | 1-Me-4-OH-4-Ph-tetrahydrothiopyranium | H | 238–240 | 2.00–2.15(2H, m), 2.35–2.44(2H, m), 2.95–3.08(2H, m), 3.69(3H, s), 5.02–5.18(2H, m), 5.42(2H, s), 5.60(1H, brs), 6.82(2H, d, J=8.1), 7.17(1H, dd, J=4.7, 7.7), 7.22–7.42(5H, m), 7.58(2H, d, J=8.1), 8.30(1H, d, J=7.7), 8.53(1H, d, J=4.7) |
| 96 | —CH$_2$— | — | Ph | Me-S$^+$(—C$_2$H$_4$—NH—C(O)—3,4,5-(MeO)$_3$-C$_6$H$_2$) | H | 172–174 | 3.19(3H, s), 3.41–3.68(2H, m), 3.70(3H, s), 3.78(6H, s), 3.79–4.09(2H, m), 5.41(2H, s), 7.10–7.29(8H, m), 8.24(1H, d, J=7.7), 8.46(1H, d, J=4.7), 8.63(1H, brs) |

TABLE 2-continued

| No. | A | R$^1$ | R$^2$ | R$^3$ | | R$^7$ | m.p. (° C.) | $^1$H-NMR (δ: ppm) |
|---|---|---|---|---|---|---|---|---|
| 97 | —CH$_2$— | — | | ⟨OMe-phenyl⟩ | Me—S$^+$—C$_2$H$_4$—NH—C(O)—⟨3,4,5-triOMe-phenyl⟩ | H | 180–182 | 3.18(3H, s), 3.40–3.65(2H, m), 3.68(3H, s), 3.70 (3H, s), 3.79(6H, m), 3.80–4.09(2H, m), 5.34(2H, s), 6.79(2H, d, J=8.7), 7.13(1H, dd, J=4.7, 7.7), 7.14(2H, s), 7.22(2H, d, J=8.7), 8.23(1H, d, J=7.7), 8.49(1H, d, J=4.7), 8.64(1H, brs) |
| 98 | —CH$_2$— | — | Ph | | Me—S$^+$—C$_2$H$_4$—O—C(O)—⟨3,4,5-triOMe-phenyl⟩ | H | 125–127 | 2.65–2.75(2H, m), 3.19(3H, s), 3.30–3.41(1H, m), 3.60(3H, s), 3.68(6H, s), 4.15–4.25(1H, m), 5.44 (2H, s), 6.88(2H, s), 7.10–7.27(6H, m), 8.25(1H, d, J=7.7), 8.47(1H, d, J=4.7), 9.98(1H, brs) |
| 99 | —CH$_2$— | — | Ph | | Me—S$^+$—C$_3$H$_6$—O—C(O)—⟨3,4,5-triOMe-phenyl⟩ | H | 183–184 | 2.00–2.10(2H, m), 3.19(3H, s), 3.41–3.55(1H, m), 3.74(3H, s), 3.81(6H, s), 4.15–4.36(3H, m), 5.42 (2H, s), 7.10–7.27(8H, m), 8.20(1H, d, J=7.7), 8.46(1H, d, J=4.7) |
| 100 | —CH$_2$— | — | Ph | | Me—S$^+$—C$_3$H$_6$—NH—C(O)—⟨3,4,5-triOMe-phenyl⟩ | H | 89–92 | 1.73–1.89(2H, m), 3.15(3H, s), 3.30–3.41(3H, m), 3.70(3H, s), 3.80(6H, s), 3.97–3.09(1H, m), 5.46 (2H, s), 7.11–7.27(8H, m), 8.25(1H, d, J=7.9), 8.48(1H, d, J=4.7) |

TABLE 2-continued

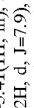

| No. | A | R¹ | R² | R³ | R⁷ | m.p. (° C.) | ¹H-NMR (δ: ppm) |
|-----|-----|-----|-----|-----|-----|-----|-----|
| 101 | —CH₂— | — | 4-MeO-C₆H₄ | Me—S-n-Pr⁺ | H | 147—149 | 1.04(3H, t, J=7.4), 1.51–1.80(2H, m), 2.29(3H, s), 3.19(3H, s), 3.30–3.41(1H, m), 3.97–4.09(1H, m), 5.50(2H, s), 7.11(2H, d, J=7.9), 7.19(2H, d, J=7.9), 7.21(1H, dd, J=4.5, 7.9), 8.33(1H, d, J=7.9), 8.56 (1H, d, J=4.5) |
| 102 | —CH₂— | — | 4-MeO-C₆H₄ | Me—S-n-Pr⁺ | H | 121—122 | 0.97(3H, t, J=7.4), 1.43–1.72(2H, m), 3.12(3H, s), 3.23–3.34(1H, m), 3.69(3H, s), 3.90–4.02(1H, m), 5.40(2H, s), 6.81(2H, d, J=8.6), 7.16(2H, dd, J=4.7, 7.4), 7.22(2H, d, J=8.6), 8.27(1H, d, J=7.4), 8.51(1H, d, J=4.7) |
| 103 | —CH₂— | — | 3,4-diMe-C₆H₃ | Me—S-n-Pr⁺ | H | 156—157 | 0.97(3H, t, J=7.4), 1.42–1.73(2H, m), 2.18(3H, s), 2.37(3H, s), 3.12(3H, s), 3.22–3.37(1H, m), 3.93–4.03(1H, m), 5.37(2H, s), 6.48(1H, d, J=7.9), 6.77 (1H, d, J=7.9), 6.98(1H, s), 7.16(1H, dd, J=4.7, 7.7), 8.29(1H, d, J=7.7), 8.44(1H, d, J=4.7) |
| 104 | —CH₂— | — | 3-Me-C₆H₄ | Me—S-n-Pr⁺ | H | 135—136 | 0.97(3H, t, J=7.4), 1.45–1.73(2H, m), 2.22(3H, s), 3.13(3H, s), 3.21–3.40(1H, m), 3.93–4.04(1H, m), 5.45(2H, s), 6.94–7.03(3H, m), 7.08–7.19(2H, m), 8.28(1H, d, J=7.7), 8.49(1H, d, J=4.7) |
| 105 | —CH₂— | — | 2-Me-C₆H₄ | Me—S-n-Pr⁺ | H | 175—177 | 0.97(3H, t, J=7.4), 1.45–1.75(2H, m), 2.41(3H, s), 3.13(3H, s), 3.20–3.39(1H, m), 3.91–4.04(1H, m), 5.41(2H, s), 6.58(1H, d, J=7.8), 6.91–7.20(4H, m), 8.30(1H, d, J=7.4), 8.44(1H, d, J=4.7) |

TABLE 2-continued
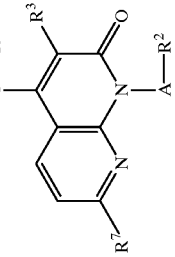
| No. | A | R¹ | R² | R³ | | R⁷ | m.p. (° C.) | ¹H-NMR (δ: ppm) |
|---|---|---|---|---|---|---|---|---|
| 106 | —CH₂— | — |  | Me— | —S-n-Pr⁺ | H | 110–112 | 0.97(3H, t, J=7.4), 1.45–1.73(2H, m), 2.13(3H, s), 3.13(3H, s), 3.20–3.38(1H, m), 3.91–4.04(1H, m), 5.40(2H, s), 6.80–7.03(3H, m), 7.15(1H, dd, J=4.7, 7.9), 8.27(1H, d, J=7.9), 8.49(1H, d, J=4.7) |
| 107 | —CH₂— | — |  | Me— | —S-n-Pr⁺ | H | 98–99 | 0.97(3H, t, J=7.4), 1.43–1.73(2H, m), 3.13(3H, s), 3.21–3.33(1H, m), 3.68(1H, s), 3.91–4.03(1H, m), 5.45(2H, s), 6.71–6.81(3H, m), 7.10–7.21(2H, m), 8.27(1H, d, J=7.7), 8.50(1H, d, J=4.7) |
| 108 | —CH₂— | — | 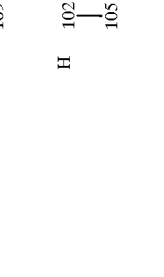 | Me— | —S-n-Pr⁺ | H | 150–152 | 0.97(3H, t, J=7.4), 1.14(6H, d, J=6.9), 1.47–1.71(2H, m), 2.73–2.90(1H, m), 3.13(3H, s), 3.27–3.40(1H, m), 3.93–4.04(1H, m), 5.44(2H, s), 7.08–7.20(5H, m), 8.28(1H, d, J=7.4), 8.50(1H, d, J=4.9) |
| 109 | —CH₂— | — | 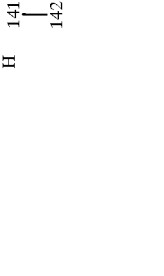 | Me— | —S-n-Pr⁺ | H | 168–169 | 0.97(3H, t, J=7.4), 1.22(9H, s), 1.44–1.72(2H, m), 3.13(3H, s), 3.23–3.40(1H, m), 3.91–4.03(1H, m), 5.44(2H, s), 7.13–7.19(3H, m), 7.26(2H, d, J=7.9), 8.28(1H, d, J=7.9), 8.50(1H, d, J=4.5) |
| 110 | —CH₂— | — |  | Me— | —S-n-Pr⁺ | H | 102–105 | 0.97(3H, t, J=7.4), 1.47–1.72(2H, m), 3.13(3H, s), 3.23–3.33(1H, m), 3.90–4.01(1H, m), 5.51(2H, s), 6.66(1H, d, J=9.4), 7.17–7.23(2H, m), 7.50(1H, d, J=7.4), 8.32(1H, d, J=7.7), 8.45(1H, d, J=4.7) |
| 111 | —CH₂— | — |  | Me— | —S-n-Pr⁺ | H | 141–142 | 0.97(3H, t, J=7.4), 1.43–1.73(2H, m), 3.13(3H, s), 3.25–3.35(1H, m), 3.91–4.02(1H, m), 5.45(2H, s), 7.01–7.10(2H, m), 7.18(1H, dd, J=4.7, 7.7), 7.25–7.36(2H, m), 8.28(1H, d, J=7.7), 8.51(1H, d, J=4.7) |

TABLE 2-continued

[Structure: quinoline-like scaffold with O-R¹, R³, =O, N-A-R², and R⁷ substituents]

| No. | A | R¹ | R² | R³ | R⁷ | m.p. (° C.) | ¹H-NMR (δ: ppm) |
|---|---|---|---|---|---|---|---|
| 112 | —CH₂— | — | 1-naphthyl-methyl | Me, —S-n-Pr+ | H | 200–202 | 0.98(3H, t, J=7.4), 1.48–1.75(2H, m), 3.15(3H, s), 3.21–3.33(1H, m), 3.93–4.04(1H, m), 5.95(2H, s), 6.77(1H, d, J=7.4), 7.17(1H, dd, J=4.7, 7.7), 7.29(1H, dd, J=7.4, 7.9), 7.53–7.70(2H, m), 7.76(1H, d, J=8.2), 7.96(1H, d, J=7.9), 8.28(1H, d, J=8.2), 8.33(1H, d, J=7.7), 8.39(1H, d, J=4.7) |
| 113 | —CH₂— | — | 4-pyridyl-methyl | Me, —S-n-Pr+ | H | 168–169 | 0.97(3H, t, J=7.4), 1.45–1.71(2H, m), 3.14(3H, s), 3.23–3.32(1H, m), 3.91–4.02(1H, m), 5.49(2H, s), 7.15(2H, d, J=4.9), 7.19(1H, dd, J=4.7, 7.7), 8.30(1H, d, J=7.7), 8.43(2H, d, J=4.9), 8.46(1H, d, J=4.7) |
| 114 | —CH₂— | — | 4-phenyl-phenyl-methyl | Me, —S-n-Pr+ | H | 146–147 | 0.98(3H, t, J=7.4), 1.45–1.74(2H, m), 3.14(3H, s), 3.23–3.33(1H, m), 3.91–4.03(1H, m), 5.53(2H, s), 7.18(1H, dd, J=4.7, 7.7), 7.28–7.35(3H, m), 7.38–7.47(2H, m), 7.51–7.65(4H, m), 8.30(1H, d, J=7.7), 8.52(1H, d, J=4.7) |
| 115 | —CH₂— | — | 3-pyridyl-methyl | Me, —S-n-Pr+ | H | 59–61 | 0.97(3H, t, J=7.4), 1.45–1.70(2H, m), 3.13(3H, s), 3.20–3.31(1H, m), 3.91–4.05(1H, m), 5.49(2H, s), 7.19(1H, dd, J=4.8, 7.6), 7.29(1H, dd, J=4.8, 7.9), 7.64(1H, d, J=7.9), 8.28(1H, d, J=7.6), 8.40(1H, d, J=4.8), 8.50–8.59(2H, m) |
| 116 | —CH₂— | — | 4-(OCF₃)-phenyl-methyl | Me, —S-n-Pr+ | H | 111–113 | 0.96(3H, t, J=7.4), 1.45–1.70(2H, m), 3.12(3H, s), 3.20–3.30(1H, m), 3.91–4.03(1H, m), 5.49(2H, s), 7.19(1H, dd, J=4.6, 7.6), 7.26(2H, d, J=8.4), 7.36(2H, d, J=8.4), 8.29(1H, d, J=7.6), 8.51(1H, d, J=4.6) |

EXAMPLES 117–308

The compounds shown in Table 3 are synthesized using appropriate starting compounds and carrying out the reactions as shown in one of the above Examples.

TABLE 3

| No. | A | $R^1$ | $R^2$ | $R^3$ | $R^7$ |
|---|---|---|---|---|---|
| 117 | —$C_2H_4$— | — | 4-Cl-C6H4 | Me-S(+)-n-Pr | H |
| 118 | —$C_2H_4$— | — | 3,4-(OMe)2-C6H3 | Me-S(+)-n-Pr | H |
| 119 | —$C_2H_4$— | — | 3,4,5-(OMe)3-C6H2 | Me-S(+)-n-Pr | H |
| 120 | —$C_2H_4$— | — | 4-OMe-C6H4 | Me-S(+)-n-Pr | H |
| 121 | —$C_2H_4$— | — | 4-Me-C6H4 | Me-S(+)-n-Pr | H |
| 122 | —$C_2H_4$— | — | 4-pyridyl | Me-S(+)-n-Pr | H |
| 123 | —$CH_2$— | — | 4-Cl-C6H4 | Me-S(+)-n-Pr | Me |
| 124 | —$CH_2$— | — | 3,4-(OMe)2-C6H3 | Me-S(+)-n-Pr | Me |
| 125 | —$CH_2$— | — | 4-OMe-C6H4 | Me-S(+)-n-Pr | Me |

TABLE 3-continued

[Structure: 1,8-naphthyridinone core with O-R¹ at 4-position, R³ at 3-position, R⁷ at 7-position, and A-R² on N1, C=O at 2-position]

| No. | A | R¹ | R² | R³ | R⁷ |
|---|---|---|---|---|---|
| 126 | —CH₂— | — | 4-Me-C₆H₄— | —S⁺(Me)-n-Pr | Me |
| 127 | —CH₂— | — | 4-pyridyl— | —S⁺(Me)-n-Pr | Me |
| 128 | —C₂H₄— | — | Ph | —S⁺(Me)-n-Pr | Me |
| 129 | —C₂H₄— | — | 4-Cl-C₆H₄— | —S⁺(Me)-n-Pr | Me |
| 130 | —C₂H₄— | — | 3,4-(OMe)₂-C₆H₃— | —S⁺(Me)-n-Pr | Me |
| 131 | —C₂H₄— | — | 3,4,5-(OMe)₃-C₆H₂— | —S⁺(Me)-n-Pr | Me |
| 132 | —C₂H₄— | — | 4-OMe-C₆H₄— | —S⁺(Me)-n-Pr | Me |
| 133 | —C₂H₄— | — | 4-Me-C₆H₄— | —S⁺(Me)-n-Pr | Me |
| 134 | —C₂H₄— | — | 4-pyridyl— | —S⁺(Me)-n-Pr | Me |
| 135 | —CH₂— | — | 4-Cl-C₆H₄— | —S⁺(Me)-C₂H₄-C(O)-Me | H |
| 136 | —CH₂— | — | 3,4-(OMe)₂-C₆H₃— | —S⁺(Me)-C₂H₄-C(O)-Me | H |

TABLE 3-continued
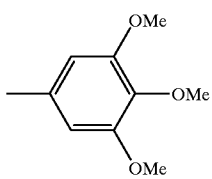
| No. | A | R¹ | R² | R³ | R⁷ |
|---|---|---|---|---|---|
| 137 | —CH₂— | — | 3,4,5-(OMe)₃-C₆H₂— | —S⁺(Me)—C₂H₄—C(O)—Me | H |
| 138 | —CH₂— | — | 4-OMe-C₆H₄— | —S⁺(Me)—C₂H₄—C(O)—Me | H |
| 139 | —CH₂— | — | 4-Me-C₆H₄— | —S⁺(Me)—C₂H₄—C(O)—Me | H |
| 140 | —CH₂— | — | 4-pyridyl | —S⁺(Me)—C₂H₄—C(O)—Me | H |
| 141 | —C₂H₄— | — | Ph | —S⁺(Me)—C₂H₄—C(O)—Me | H |
| 142 | —C₂H₄— | — | 4-Cl-C₆H₄— | —S⁺(Me)—C₂H₄—C(O)—Me | H |
| 143 | —C₂H₄— | — | 3,4-(OMe)₂-C₆H₃— | —S⁺(Me)—C₂H₄—C(O)—Me | H |
| 144 | —C₂H₄— | — | 3,4,5-(OMe)₃-C₆H₂— | —S⁺(Me)—C₂H₄—C(O)—Me | H |
| 145 | —C₂H₄— | — | 4-OMe-C₆H₄— | —S⁺(Me)—C₂H₄—C(O)—Me | H |
| 146 | —C₂H₄— | — | 4-Me-C₆H₄— | —S⁺(Me)—C₂H₄—C(O)—Me | H |

TABLE 3-continued
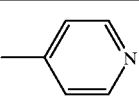
| No. | A | R¹ | R² | R³ | R⁷ |
|---|---|---|---|---|---|
| 147 | —C₂H₄— | — | 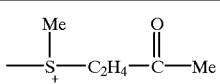 |  | H |
| 148 | —CH₂— | — | Ph | 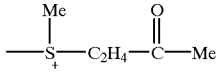 | Me |
| 149 | —CH₂— | — |  |  | Me |
| 150 | —CH₂— | — | 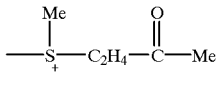 |  | Me |
| 151 | —CH₂— | — | 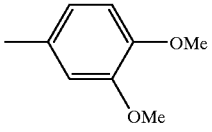 | 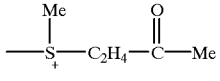 | Me |
| 152 | —CH₂— | — |  | 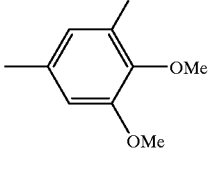 | Me |
| 153 | —CH₂— | — | 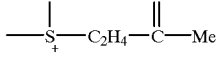 |  | Me |
| 154 | —CH₂— | — | 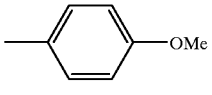 | 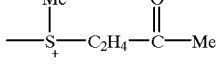 | Me |
| 155 | —CH₂— | — | Ph |  | Me |
| 156 | —C₂H₄— | — | 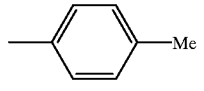 | 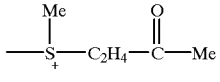 | Me |
| 157 | —C₂H₄— | — |  | 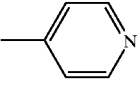 | Me |

TABLE 3-continued
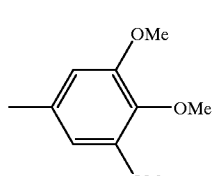
| No. | A | R¹ | R² | R³ | R⁷ |
|---|---|---|---|---|---|
| 158 | —C₂H₄— | — | 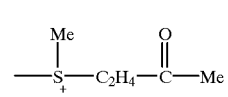 3,4,5-(OMe)₃-C₆H₂— | 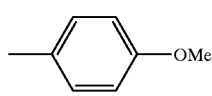 —S⁺(Me)—C₂H₄—C(O)—Me | Me |
| 159 | —C₂H₄— | — | 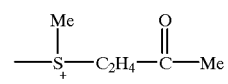 4-OMe-C₆H₄— | 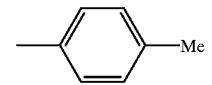 —S⁺(Me)—C₂H₄—C(O)—Me | Me |
| 160 | —C₂H₄— | — | 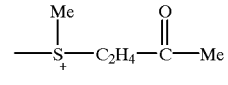 4-Me-C₆H₄— | 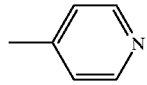 —S⁺(Me)—C₂H₄—C(O)—Me | Me |
| 161 | —C₂H₄— | — | 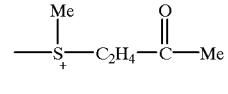 4-pyridyl |  —S⁺(Me)—C₂H₄—C(O)—Me | Me |
| 162 | —CH₂— | — | 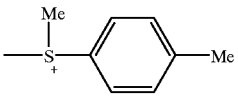 4-Cl-C₆H₄— | 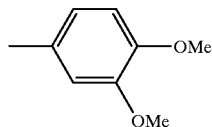 —S⁺(Me)—C₆H₄-4-Me | H |
| 163 | —CH₂— | — | 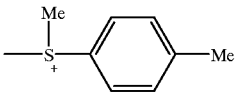 3,4-(OMe)₂-C₆H₃— | 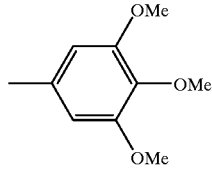 —S⁺(Me)—C₆H₄-4-Me | H |
| 164 | —CH₂— | — | 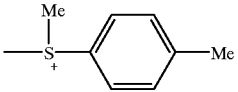 3,4,5-(OMe)₃-C₆H₂— | 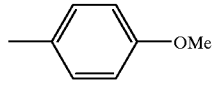 —S⁺(Me)—C₆H₄-4-Me | H |
| 165 | —CH₂— | — | 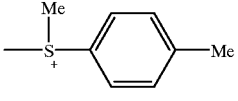 4-OMe-C₆H₄— | 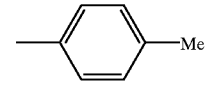 —S⁺(Me)—C₆H₄-4-Me | H |
| 166 | —CH₂— | — | 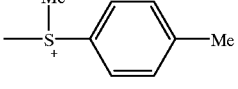 4-Me-C₆H₄— | 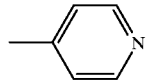 —S⁺(Me)—C₆H₄-4-Me | H |
| 167 | —CH₂— | — | 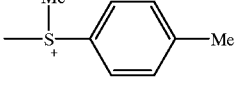 4-pyridyl | —S⁺(Me)—C₆H₄-4-Me | H |

TABLE 3-continued
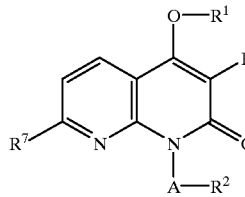
| No. | A | R¹ | R² | R³ | R⁷ |
|---|---|---|---|---|---|
| 168 | —C₂H₄— | — | Ph | 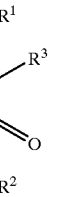 | H |
| 169 | —C₂H₄— | — | 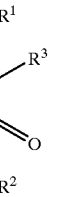 | 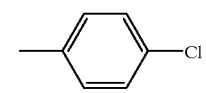 | H |
| 170 | —C₂H₄— | — |  |  | H |
| 171 | —C₂H₄— | — |  | 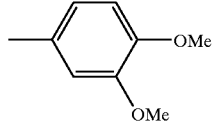 | H |
| 172 | —C₂H₄— | — |  |  | H |
| 173 | —C₂H₄— | — |  | 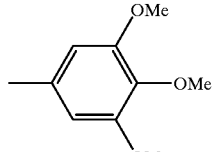 | H |
| 174 | —C₂H₄— | — |  |  | H |
| 175 | —CH₂— | — |  | 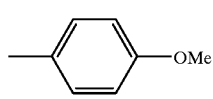 | Me |
| 176 | —CH₂— | — |  |  | Me |

TABLE 3-continued

| No. | A | R¹ | R² | R³ | R⁷ |
|---|---|---|---|---|---|
| 177 | —CH₂— | — | 3,4,5-(MeO)₃-C₆H₂— | —S⁺(Me)(4-Me-C₆H₄) | Me |
| 178 | —CH₂— | — | 4-MeO-C₆H₄— | —S⁺(Me)(4-Me-C₆H₄) | Me |
| 179 | —CH₂— | — | 4-Me-C₆H₄— | —S⁺(Me)(4-Me-C₆H₄) | Me |
| 180 | —CH₂— | — | 4-pyridyl | —S⁺(Me)(4-Me-C₆H₄) | Me |
| 181 | —C₂H₄— | — | Ph | —S⁺(Me)(4-Me-C₆H₄) | Me |
| 182 | —C₂H₄— | — | 4-Cl-C₆H₄— | —S⁺(Me)(4-Me-C₆H₄) | Me |
| 183 | —C₂H₄— | — | 3,4-(MeO)₂-C₆H₃— | —S⁺(Me)(4-Me-C₆H₄) | Me |
| 184 | —C₂H₄— | — | 3,4,5-(MeO)₃-C₆H₂— | —S⁺(Me)(4-Me-C₆H₄) | Me |
| 185 | —C₂H₄— | — | 4-MeO-C₆H₄— | —S⁺(Me)(4-Me-C₆H₄) | Me |
| 186 | —C₂H₄— | — | 4-Me-C₆H₄— | —S⁺(Me)(4-Me-C₆H₄) | Me |

TABLE 3-continued

| No. | A | R¹ | R² | R³ | R⁷ |
|---|---|---|---|---|---|
| 187 | —C₂H₄— | — | 4-pyridyl | S-Me⁺ -C₆H₄-4-Me (Me) | Me |
| 188 | —CH₂— | — | 4-Cl-C₆H₄ | thianyl S⁺ | H |
| 189 | —CH₂— | — | 3,4-(OMe)₂-C₆H₃ | thianyl S⁺ | H |
| 190 | —CH₂— | — | 3,4,5-(OMe)₃-C₆H₂ | thianyl S⁺ | H |
| 191 | —CH₂— | — | 4-OMe-C₆H₄ | thianyl S⁺ | H |
| 192 | —CH₂— | — | 4-Me-C₆H₄ | thianyl S⁺ | H |
| 193 | —CH₂— | — | 4-pyridyl | thianyl S⁺ | H |
| 194 | —C₂H₄— | — | Ph | thianyl S⁺ | H |
| 195 | —C₂H₄— | — | 4-Cl-C₆H₄ | thianyl S⁺ | H |
| 196 | —C₂H₄— | — | 3,4-(OMe)₂-C₆H₃ | thianyl S⁺ | H |

TABLE 3-continued
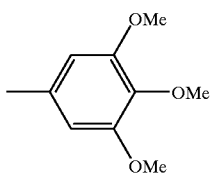
| No. | A | R¹ | R² | R³ | R⁷ |
|---|---|---|---|---|---|
| 197 | —C₂H₄— | — | 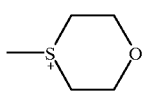 3,4,5-tri-OMe phenyl | 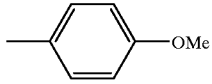 | H |
| 198 | —C₂H₄— | — | 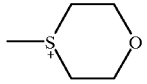 4-OMe phenyl | 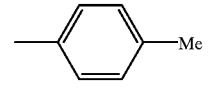 | H |
| 199 | —C₂H₄— | — | 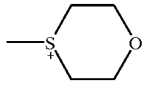 4-Me phenyl | 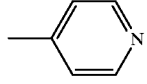 | H |
| 200 | —CH₂— | — | 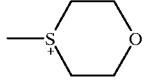 4-pyridyl | 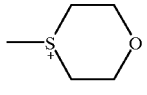 | H |
| 201 | —CH₂— | — | Ph | 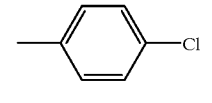 | Me |
| 202 | —CH₂— | — | 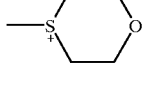 4-Cl phenyl | 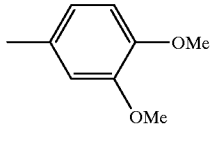 | Me |
| 203 | —CH₂— | — | 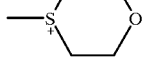 3,4-di-OMe phenyl | 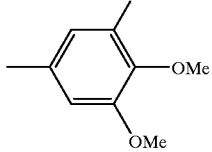 | Me |
| 204 | —CH₂— | — | 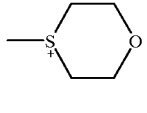 3,4,5-tri-OMe phenyl | 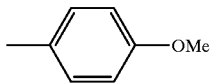 | Me |
| 205 | —CH₂— | — | 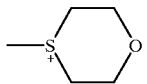 4-OMe phenyl | 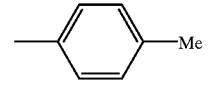 | Me |
| 206 | —CH₂— | — | 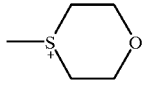 4-Me phenyl | | Me |

TABLE 3-continued

Core structure: 4-(OR¹)-3-R³-7-R⁷-1-(A-R²)-1,8-naphthyridin-2(1H)-one

| No. | A | R¹ | R² | R³ | R⁷ |
|---|---|---|---|---|---|
| 207 | —CH₂— | — | 4-pyridyl | thian-4-ium-4-yl (1,4-thioxanium, S⁺ in ring with O) | Me |
| 208 | —C₂H₄— | — | Ph | thian-4-ium-4-yl (S⁺/O ring) | Me |
| 209 | —C₂H₄— | — | 4-Cl-C₆H₄— | thian-4-ium-4-yl (S⁺/O ring) | Me |
| 210 | —C₂H₄— | — | 3,4-(OMe)₂-C₆H₃— | thian-4-ium-4-yl (S⁺/O ring) | Me |
| 211 | —C₂H₄— | — | 3,4,5-(OMe)₃-C₆H₂— | thian-4-ium-4-yl (S⁺/O ring) | Me |
| 212 | —C₂H₄— | — | 4-OMe-C₆H₄— | thian-4-ium-4-yl (S⁺/O ring) | Me |
| 213 | —C₂H₄— | — | 4-Me-C₆H₄— | thian-4-ium-4-yl (S⁺/O ring) | Me |
| 214 | —C₂H₄— | — | 4-pyridyl | thian-4-ium-4-yl (S⁺/O ring) | Me |
| 215 | —CH₂— | — | 4-Cl-C₆H₄— | —S⁺(Me)—C₂H₄—O—C(O)—Me | H |
| 216 | —CH₂— | — | 4-Me-C₆H₄— | —S⁺(Me)—C₂H₄—O—C(O)—Me | H |
| 217 | —CH₂— | — | 4-pyridyl | —S⁺(Me)—C₂H₄—O—C(O)—Me | H |

TABLE 3-continued

[Structure: 1,8-naphthyridine core with O-R¹ at position 4, R³ at position 3, =O at position 2, A-R² on N1, R⁷ at position 7]

| No. | A | R¹ | R² | R³ | R⁷ |
|---|---|---|---|---|---|
| 218 | —C₂H₄— | — | Ph | —S⁺(Me)—C₂H₄—O—C(O)—Me | H |
| 219 | —C₂H₄— | — | 4-Cl-C₆H₄ | —S⁺(Me)—C₂H₄—O—C(O)—Me | H |
| 220 | —C₂H₄— | — | 3,4-(OMe)₂-C₆H₃ | —S⁺(Me)—C₂H₄—O—C(O)—Me | H |
| 221 | —C₂H₄— | — | 3,4,5-(OMe)₃-C₆H₂ | —S⁺(Me)—C₂H₄—O—C(O)—Me | H |
| 222 | —C₂H₄— | — | 4-OMe-C₆H₄ | —S⁺(Me)—C₂H₄—O—C(O)—Me | H |
| 223 | —C₂H₄— | — | 4-Me-C₆H₄ | —S⁺(Me)—C₂H₄—O—C(O)—Me | H |
| 224 | —C₂H₄— | — | 4-pyridyl | —S⁺(Me)—C₂H₄—O—C(O)—Me | H |
| 225 | —CH₂— | — | 4-Cl-C₆H₄ | —S⁺(Me)—C₂H₄—O—C(O)—Me | Me |
| 226 | —CH₂— | — | 3,4-(OMe)₂-C₆H₃ | —S⁺(Me)—C₂H₄—O—C(O)—Me | Me |
| 227 | —CH₂— | — | 4-OMe-C₆H₄ | —S⁺(Me)—C₂H₄—O—C(O)—Me | Me |
| 228 | —CH₂— | — | 4-Me-C₆H₄ | —S⁺(Me)—C₂H₄—O—C(O)—Me | Me |

TABLE 3-continued
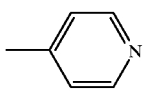
| No. | A | R¹ | R² | R³ | R⁷ |
|-----|---|-----|-----|-----|-----|
| 229 | —CH₂— | — | 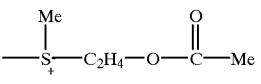 |  | Me |
| 230 | —C₂H₄— | — | Ph | 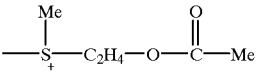 | Me |
| 231 | —C₂H₄— | — |  | 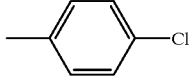 | Me |
| 232 | —C₂H₄— | — | 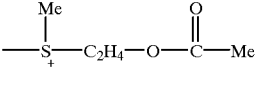 |  | Me |
| 233 | —C₂H₄— | — | 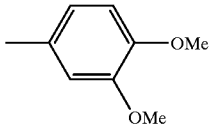 | 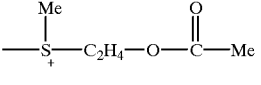 | Me |
| 234 | —C₂H₄— | — |  | 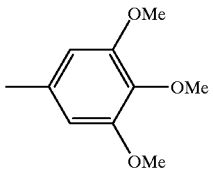 | Me |
| 235 | —C₂H₄— | — | 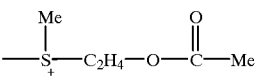 |  | Me |
| 236 | —C₂H₄— | — | 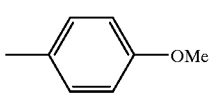 | 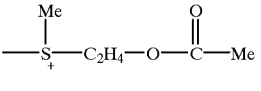 | Me |
| 237 | —CH₂— | — |  | 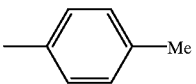 | H |

TABLE 3-continued

| No. | A | R¹ | R² | R³ | R⁷ |
|-----|---|----|----|----|----|
| 238 | —CH₂— | — | 3,4-dimethoxyphenyl | —S⁺(Me)—C₂H₄—O—C(O)—(3,4,5-trimethoxyphenyl) | H |
| 239 | —CH₂— | — | 3,4,5-trimethoxyphenyl | —S⁺(Me)—C₂H₄—O—C(O)—(3,4,5-trimethoxyphenyl) | H |
| 240 | —CH₂— | — | 4-methylphenyl | —S⁺(Me)—C₂H₄—O—C(O)—(3,4,5-trimethoxyphenyl) | H |
| 241 | —CH₂— | — | 4-pyridyl | —S⁺(Me)—C₂H₄—O—C(O)—(3,4,5-trimethoxyphenyl) | H |
| 242 | —C₂H₄— | — | Ph | —S⁺(Me)—C₂H₄—O—C(O)—(3,4,5-trimethoxyphenyl) | H |
| 243 | —C₂H₄— | — | 4-chlorophenyl | —S⁺(Me)—C₂H₄—O—C(O)—(3,4,5-trimethoxyphenyl) | H |
| 244 | —C₂H₄— | — | 3,4-dimethoxyphenyl | —S⁺(Me)—C₂H₄—O—C(O)—(3,4,5-trimethoxyphenyl) | H |

TABLE 3-continued

[Structure: 1,8-naphthyridin-2-one core with O-R¹ at 4-position, R³ at 3-position, R⁷ at 7-position, and A-R² on N1]

| No. | A | R¹ | R² | R³ | R⁷ |
|---|---|---|---|---|---|
| 245 | —C₂H₄— | — | 3,4,5-trimethoxyphenyl | —S⁺(Me)—C₂H₄—O—C(O)—(3,4,5-trimethoxyphenyl) | H |
| 246 | —C₂H₄— | — | 4-methoxyphenyl | —S⁺(Me)—C₂H₄—O—C(O)—(3,4,5-trimethoxyphenyl) | H |
| 247 | —C₂H₄— | — | 4-methylphenyl | —S⁺(Me)—C₂H₄—O—C(O)—(3,4,5-trimethoxyphenyl) | H |
| 248 | —C₂H₄— | — | 4-pyridyl | —S⁺(Me)—C₂H₄—O—C(O)—(3,4,5-trimethoxyphenyl) | H |
| 249 | —CH₂— | — | Ph | —S⁺(Me)—C₂H₄—O—C(O)—(3,4,5-trimethoxyphenyl) | Me |
| 250 | —CH₂— | — | 4-chlorophenyl | —S⁺(Me)—C₂H₄—O—C(O)—(3,4,5-trimethoxyphenyl) | Me |
| 251 | —CH₂— | — | 3,4-dimethoxyphenyl | —S⁺(Me)—C₂H₄—O—C(O)—(3,4,5-trimethoxyphenyl) | Me |

TABLE 3-continued
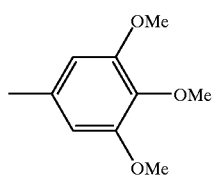
| No. | A | R¹ | R² | R³ | R⁷ |
|---|---|---|---|---|---|
| 252 | —CH₂— | — | 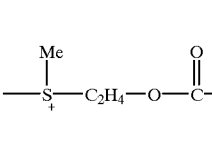 | 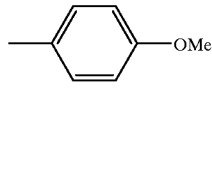 | Me |
| 253 | —CH₂— | — | 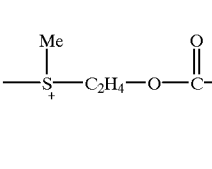 | 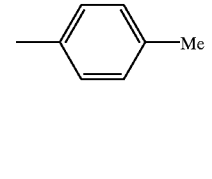 | Me |
| 254 | —CH₂— | — | 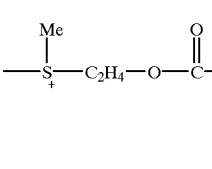 | 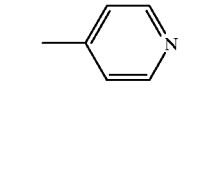 | Me |
| 255 | —CH₂— | — | 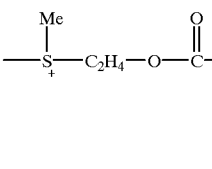 | 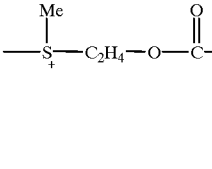 | Me |
| 256 | —C₂H₄— | — | Ph | 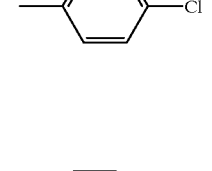 | Me |
| 257 | —C₂H₄— | — | 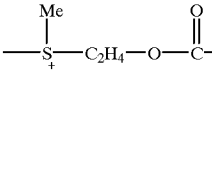 | 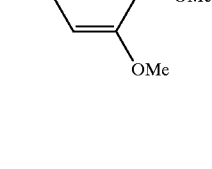 | Me |
| 258 | —C₂H₄— | — | 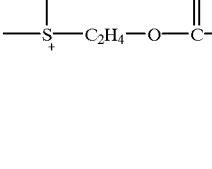 |  | Me |

TABLE 3-continued
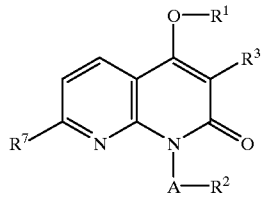
| No. | A | R¹ | R² | R³ | R⁷ |
|---|---|---|---|---|---|
| 259 | —C₂H₄— | — | 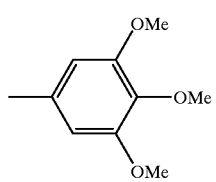 | 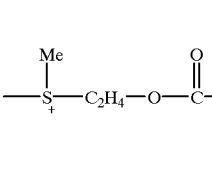 | Me |
| 260 | —C₂H₄— | — | 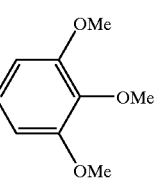 | 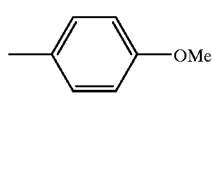 | Me |
| 261 | —C₂H₄— | — | 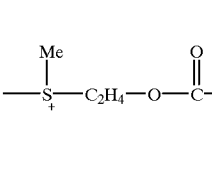 | 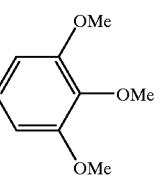 | Me |
| 262 | —C₂H₄— | — | 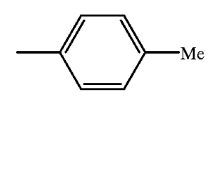 | 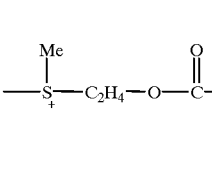 | Me |
| 263 | —CH₂— | — | 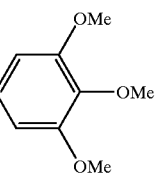 | 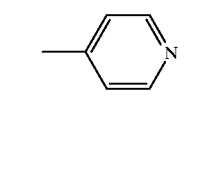 | H |
| 264 | —CH₂— | — | 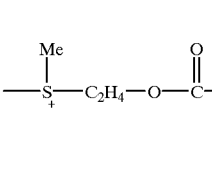 | 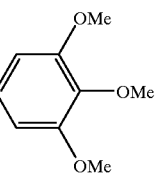 | H |
| 265 | —CH₂— | — | 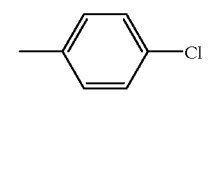 | 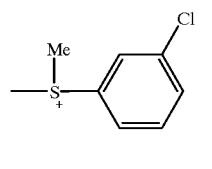 | H |

TABLE 3-continued
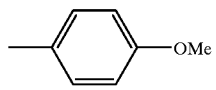
| No. | A | R¹ | R² | R³ | R⁷ |
|---|---|---|---|---|---|
| 266 | —CH₂— | — | 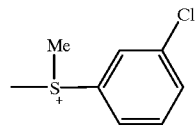 4-OMe-phenyl | 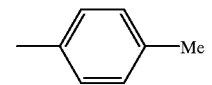 Me, S⁺, 3-Cl-phenyl | H |
| 267 | —CH₂— | — | 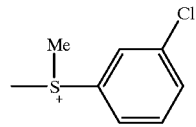 4-Me-phenyl | 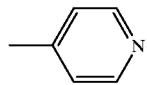 Me, S⁺, 3-Cl-phenyl | H |
| 268 | —CH₂— | — | 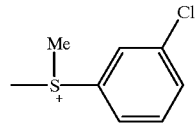 4-pyridyl | 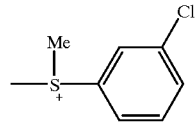 Me, S⁺, 3-Cl-phenyl | H |
| 269 | —C₂H₄— | — | Ph |  Me, S⁺, 3-Cl-phenyl | H |
| 270 | —C₂H₄— | — | 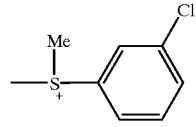 4-Cl-phenyl | 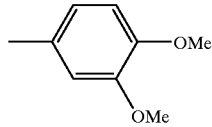 Me, S⁺, 3-Cl-phenyl | H |
| 271 | —C₂H₄— | — | 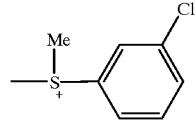 3,4-di-OMe-phenyl | 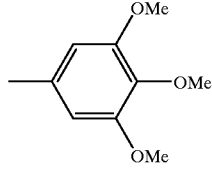 Me, S⁺, 3-Cl-phenyl | H |
| 272 | —C₂H₄— | — | 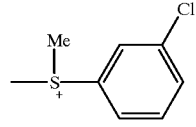 3,4,5-tri-OMe-phenyl | 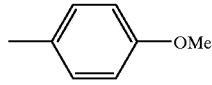 Me, S⁺, 3-Cl-phenyl | H |
| 273 | —C₂H₄— | — | 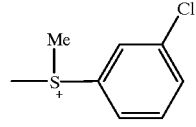 4-OMe-phenyl | Me, S⁺, 3-Cl-phenyl | H |

TABLE 3-continued
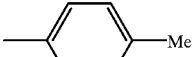
| No. | A | R¹ | R² | R³ | R⁷ |
|---|---|---|---|---|---|
| 274 | —C₂H₄— | — | 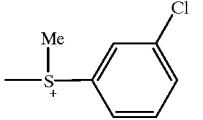 4-Me-C₆H₄ | 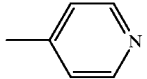 | H |
| 275 | —C₂H₄— | — | 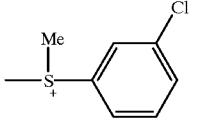 4-pyridyl | 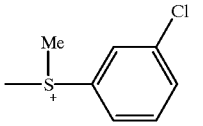 | H |
| 276 | —CH₂— | — | Ph | 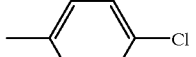 | Me |
| 277 | —CH₂— | — | 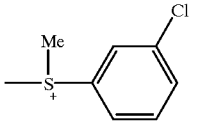 4-Cl-C₆H₄ | 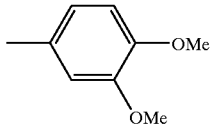 | Me |
| 278 | —CH₂— | — | 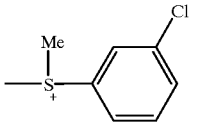 3,4-diOMe-C₆H₃ | 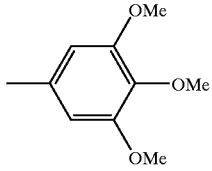 | Me |
| 279 | —CH₂— | — | 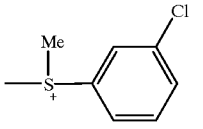 3,4,5-triOMe-C₆H₂ | 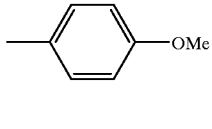 | Me |
| 280 | —CH₂— | — | 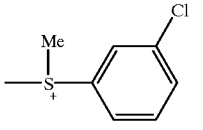 4-OMe-C₆H₄ | 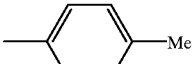 | Me |
| 281 | —CH₂— | — | 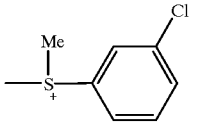 4-Me-C₆H₄ | | Me |

TABLE 3-continued
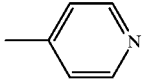
| No. | A | R¹ | R² | R³ | R⁷ |
|---|---|---|---|---|---|
| 282 | —CH₂— | — | 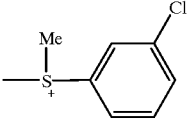 | 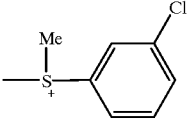 | Me |
| 283 | —C₂H₄— | — | Ph | 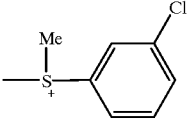 | Me |
| 284 | —C₂H₄— | — | 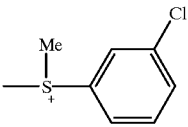 | 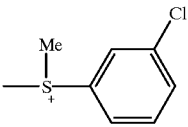 | Me |
| 285 | —C₂H₄— | — | 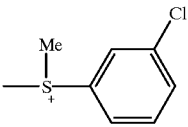 |  | Me |
| 286 | —C₂H₄— | — | 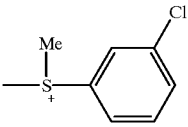 | 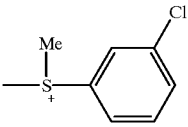 | Me |
| 287 | —C₂H₄— | — | 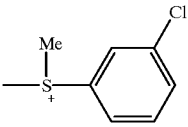 | 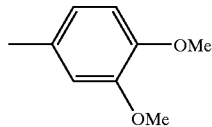 | Me |
| 288 | —C₂H₄— | — | 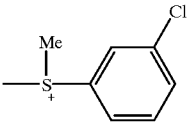 | 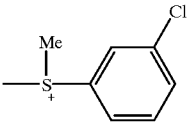 | Me |
| 289 | —C₂H₄— | — | 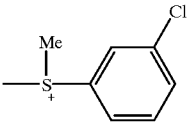 | 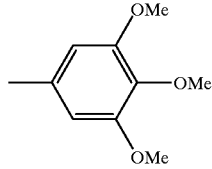 | Me |

TABLE 3-continued
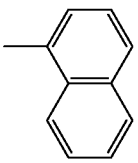
| No. | A | R¹ | R² | R³ | R⁷ |
|---|---|---|---|---|---|
| 290 | —C₃H₆— | — |  | 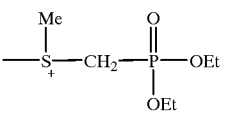 | Et |
| 291 | —CH₂— | — | 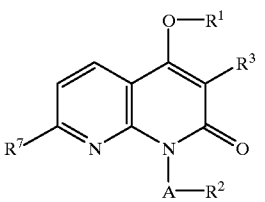 | 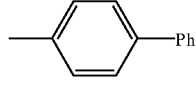 | Me |
| 292 | —C₂H₄— | — | 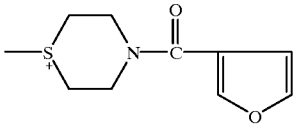 | 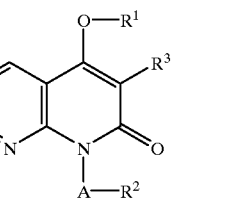 | H |
| 293 | —C₂H₄— | — | 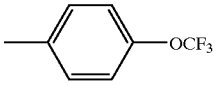 | 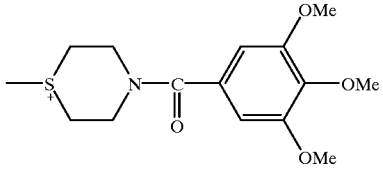 | Me |
| 294 | —C₂H₄— | — | 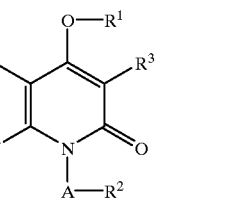 | 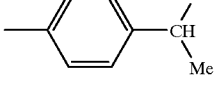 | Me |
| 295 | —CH₂— | — | 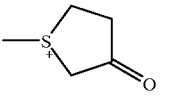 | 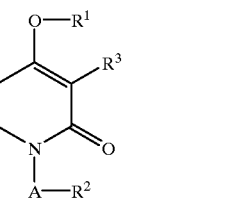 | H |
| 296 | —C₂H₄— | — | Ph | 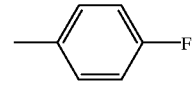 | Me |
| 297 | —C₂H₄— | — | 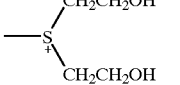 | 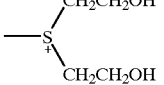 | Me |

TABLE 3-continued

| No. | A | R¹ | R² | R³ | R⁷ |
|---|---|---|---|---|---|
| 298 | —C₂H₄— | — | 2,3-dichlorophenyl | —S⁺(Me)—C₂H₄—NH—C(O)—Me | Et |
| 299 | —CH₂— | — | pyridin-3-yl | —S⁺(Me)—C₂H₄—O—C(O)—(2-methoxycarbonyl)phenyl | Me |
| 300 | —CH₂— | — | naphth-1-yl | —S⁺(Me)—C₂H₄—O—CH₂—(3,4,5-trimethoxyphenyl) | H |
| 301 | —CH₂— | — | 4-phenylphenyl | 4-phenyl-4-hydroxy-tetrahydrothiopyran-1-ium | H |
| 302 | —CH₂— | — | 4-fluorophenyl | —S⁺(Me)—C₂H₄—NH—C(O)—(3,4,5-trimethoxyphenyl) | Me |
| 303 | —C₂H₄— | — | 2,4-dimethylphenyl | —S⁺(Me)—C₂H₄—C(O)—NH—(3,4,5-trimethoxyphenyl) | H |
| 304 | —CH₂— | — | 2-chlorophenyl | —S⁺(Me)—CH₂—CH(OH)—Me | Me |
| 305 | —C₂H₄— | — | 4-(trifluoromethoxy)phenyl | —S(Me)—cyclohexyl | Me |

TABLE 3-continued

[Structure: 4-O-R¹, 3-R³, 7-R⁷, 1-A-R² substituted 1,8-naphthyridin-2-one]

| No. | A | R¹ | R² | R³ | R⁷ |
|-----|---|----|----|----|----|
| 306 | —C₄H₈— | — | Ph | —S⁺(Me)(n-Pr) | n-Bu |
| 307 | —CH₂— | — | 2-pyridyl | —C(H)(Me)(Me)—S⁺-n-Pr | Me |
| 308 | —C₂H₄— | — | 2-methylphenyl (Me) | —S⁺(Me)—CH₂—C(=O)—O—Me | Me |

Given below are Pharmacological Test Examples in which the compounds of the invention were tested and Formulation Examples in which the compounds of the invention were used.

Pharmacological Test Example 1

Using 6-week-old male S.D. rats (7 rats in each group), the pain threshold of each rat's left hind paw plantar was measured using an Analgesy-meter (product of Unicom) in accordance with the Randall-Sellitto method [Randall, L. O. and Sellitto, J. J., Arch. Int. Pharmacodyn., 111, 409 (1957)]. The values thus obtained was termed "pre-value".

One hour after the measurement of the pre-value, a 5% gum arabic suspension containing the active ingredient compound of the invention was orally administered to the rats of the test group in an amount of 10 ml/kg (so that the dosage of the active ingredient was 10 mg/kg), whereas a 5% gum arabic suspension (not containing the active ingredient compound of the invention) was orally administered to the rats of the control group in an amount of 10 ml/kg. One hour later, a physiological saline solution containing substance P (25 ng/0.1 ml) was subcutaneously injected into the left hind paw plantar of each rat.

The pain threshold of each rat's left hind paw was measured in the same manner as above at predetermined time intervals from the substance P injection (the time is shown in Table 4). The measured value is termed "post-value".

The recovery rate(%) of the pain threshold was calculated from the post-values and pre-values of the test group and control group, by means of the following formula:

Recovery Rate of Pain Threshold $$(\%) = \frac{Tb - Cb}{Ca - Cb} \times 100$$

In the formula, Tb is test group average post value, Cb is control group average post-value and Ca is control group average pre-value.

Table 4 shows the results (the highest recovery rate).

TABLE 4

| Example No. | Recovery rate (%) | Time of Measurement (minutes later) |
|-------------|-------------------|-------------------------------------|
| 1   | 58 | 60 |
| 6   | 45 | 30 |
| 7   | 37 | 60 |
| 13  | 48 | 30 |
| 14  | 41 | 60 |
| 15  | 36 | 60 |
| 22  | 44 | 60 |
| 30  | 49 | 60 |
| 33  | 23 | 30 |
| 34  | 20 | 60 |
| 47  | 95 | 60 |
| 49  | 77 | 30 |
| 64  | 66 | 60 |
| 73  | 55 | 60 |
| 89  | 71 | 60 |
| 101 | 75 | 60 |
| 102 | 73 | 60 |
| 113 | 56 | 30 |

Pharmacological Test Example 2

6-week-old male S.D. rats (7 rats in each group) were anesthetized with pentobarbital and shaved. An incision of about 3 cm in length was made in the animals' skin along the hipbone of the left hind paw to detach the musculus biceps femoris along the fascia and to expose about 1.5 cm of the sciatic nerve. The sciatic nerve was loosely ligated at four points with about 1 mm spacing from the distal end. The incision was closed with sutures.

Two weeks after the surgery, the pain threshold of the injured paw and the normal paw of each rat were measured with an Analgesy-meter (product of Muromachi Kikai K. K.) in accordance with the Randall-Sellitto method [Randall, L. O. and Sellitto, J. J., Arch. Int. Pharmacodyn., 111, 409 (1957)]. Lowered pain threshold was confirmed.

On the following day to day 7, the rats of the test group were orally given a 5% gum arabic suspension containing the active ingredient compound of the invention in an amount of 10 ml/kg once a day (the administered dosage of the active ingredient compound of the invention is shown in Table 5), whereas the rats of the control group were likewise given a 5% gum arabic suspension (not containing the active ingredient compound of the invention).

Three hours after the day 7 administration, the pain threshold of the injured paw and the normal paw of each rat were measured in the same manner as above.

The recovery rate(%) of the pain threshold was calculated from the measured values of the test group and control group, by means of the following formula:
Recovery Rate of Pain Threshold $$(\%) = \frac{Tb' - Cb'}{Ca' - Cb'} \times 100$$

In the formula, Tb' is test group injured paw average value, Cb' is control group injured paw average value and Ca' is control group normal paw average value.

TABLE 5

| Example No. | Recovery rate (%) | Dosage (mg/kg) |
|---|---|---|
| 7 | 26 | 10 |
| 33 | 18 | 10 |
| 34 | 46 | 30 |
| 102 | 15 | 10 |

Formulation Example 1 Manufacture of Tablets

Tablets (2000 tables), each containing as an active ingredient 300 mg of the compound of the invention obtained in Example 34, were manufactured according to the following formulation:
Compound of the invention obtained in Example 34 600 g
Lactose (Japanese pharmacopoeia) 67 g
Corn starch (Japanese pharmacopoeia) 33 g
Carboxymethyl cellulose calcium
(Japanese pharmacopoeia) 25 g
Methyl cellulose (Japanese pharmacopoeia) 12 g
Magnesium stearate (Japanese pharmacopoeia) 3 g More specifically, the compound of the invention obtained in Example 34, lactose, corn starch and carboxymethyl cellulose calcium were fully blended and granulated using an aqueous methyl cellulose solution. The granulated mixture was passed through a 24-mesh sieve, and the granules under the sieve were mixed with magnesium stearate and compression-molded to give the desired tablets.

Formulation Example 2 Manufacture of Capsules

Hard gelatin capsules (2000 capsules), each containing as an active ingredient 200 mg of the compound of the invention obtained in Example 7, were manufactured according to the following formulation:
Compound of the invention obtained in Example 7 400 g
Crystalline cellulose (Japanese pharmacopoeia) 60 g
Corn starch (Japanese pharmacopoeia) 34 g
Talc (Japanese pharmacopoeia) 4 g
Magnesium stearate (Japanese pharmacopoeia) 2 g More specifically, the above ingredients were finely pulverized and blended to give a homogeneous mixture. This mixture was filled into proper-sized gelatin capsule shells for oral administration to provide the desired capsules.

What is claimed is:
1. A naphthyridine compound represented by the formula (1)

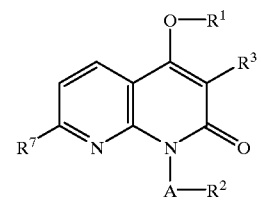

wherein A is lower alkylene;
$R^1$ is hydrogen or an electron pair "-";
$R^2$ is pyridyl; naphthyl; biphenylyl; or phenyl optionally having 1 to 3 substituents selected from the group consisting of halogen, lower alkyl, lower alkoxy and halogen-substituted lower alkoxy;
when $R^1$ is an electron pair "-", $R^3$ is a group represented by

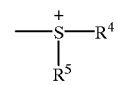

wherein $R^4$ and $R^5$ are the same or different and each represent lower alkyl, oxoalkyl, phenyl-lower alkyl, hydroxy-lower alkyl, di(lower alkyl)phosphono-lower alkyl, N-lower alkylcarbamoyl-lower alkyl, lower alkoxycarbonyl-lower alkyl, cycloalkyl, lower alkanoyloxy-lower alkyl, N-lower alkanoylamino-lower alkyl, lower alkoxy-lower alkyl, benzoyloxy-lower alkyl optionally having 1 to 3 substituents selected from the group consisting of lower alkoxy and lower alkanoyloxy on the benzene ring, N,N-di(lower alkyl)carbamoyloxy-lower alkyl, benzyloxy-lower alkyl having 1 to 3 lower alkoxy groups on the benzene ring, N-benzoylamino-lower alkyl having 1 to 3 lower alkoxy groups on the benzene ring, N-phenylcarbamoyl-lower alkyl having 1 to 3 lower alkoxy groups on the benzene ring, diphenylacetoxy-lower alkyl, or phenyl optionally having 1 to 3 substituents selected from the group consisting of lower alkyl, hydroxyl, halogen and lower alkoxy; or
$R^4$ and $R^5$ taken together form a heterocyclic ring containing the sulfur atom to which they are attached, the heterocyclic ring being optionally substituted with 2-furoyl, tri(lower alkoxy)benzoyl or oxo or with phenyl and hydroxyl;
when $R^1$ is hydrogen, $R^3$ is a group —S—$R^6$ wherein $R^6$ is lower alkyl, oxoalkyl, phenyl-lower alkyl, hydroxy-lower alkyl, di(lower alkyl)phosphono-lower alkyl, N-lower alkylcarbamoyl-lower alkyl, lower alkoxycarbonyl-lower alkyl, cycloalkyl, lower alkanoyloxy-lower alkyl, N-lower alkanoylamino-lower alkyl, lower alkoxy-lower alkyl, benzoyloxy-lower alkyl optionally having 1 to 3 substituents selected from the group consisting of lower alkoxy and lower alkanoyloxy on the benzene ring, N,N-di(lower alkyl)carbamoyloxy-lower alkyl, benzyloxy-lower alkyl having 1 to 3 lower alkoxy groups on the benzene ring, N-benzoylamino-lower alkyl having 1 to 3 lower alkoxy groups on the benzene ring, N-phenylcarbamoyl-lower alkyl having 1 to 3 lower alkoxy groups on the benzene ring, diphenylacetoxy-lower alkyl, or phenyl optionally having 1 to 3 substituents selected from the group consisting of lower alkyl, hydroxyl, halogen and lower alkoxy; and $R^7$ is hydrogen or lower alkyl.

2. The naphthyridine compound according to claim 1 wherein in the formula (1), $R^2$ is phenyl optionally having 1 to 3 substituents selected from the group consisting of halogen and lower alkyl;

when $R^1$ is an electron pair "-", $R^3$ is a group represented by

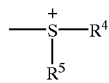

wherein $R^4$ and $R^5$ are the same or different and each represent lower alkyl, oxoalkyl, phenyl-lower alkyl, hydroxy-lower alkyl, di(lower alkyl)phosphono-lower alkyl, N-lower alkylcarbamoyl-lower alkyl, lower alkoxycarbonyl-lower alkyl, or phenyl optionally having 1 to 3 substituents selected from the group consisting of lower alkyl, hydroxyl, halogen and lower alkoxy, or $R^4$ and $R^5$ taken together form a heterocyclic ring containing the sulfur atom to which they are attached, the heterocyclic ring being optionally substituted with 2-furoyl, tri(lower alkoxy)benzoyl or oxo; when $R^1$ is hydrogen, $R^3$ is a group —S—$R^6$ wherein $R^6$ is lower alkyl, oxoalkyl, phenyl-lower alkyl, hydroxy-lower alkyl, di(lower alkyl)phosphono-lower alkyl, N-lower alkylcarbamoyl-lower alkyl, lower alkoxycarbonyl-lower alkyl, or phenyl optionally having 1 to 3 substituents selected from the group consisting of lower alkyl, hydroxyl, halogen and lower alkoxy, and $R^7$ is hydrogen.

3. The naphthyridine compound according to claim 1 or 2 wherein in the formula (1), $R^1$ is an electron pair "-", $R^4$ is lower alkyl, phenyl or hydroxy-lower alkyl, or $R^4$ and $R^5$, taken together with the sulfur atom to which they are attached, form a heterocyclic ring which is optionally substituted with 2-furoyl, tri(lower alkoxy)benzoyl or oxo.

4. The naphthyridine compound according to claim 1 or 2 wherein in the formula (1), $R^1$ is hydrogen and $R^6$ is lower alkyl or phenyl.

5. The naphthyridine compound according to claim 3 wherein in the formula (1), A is methylene.

6. The naphthyridine compound according to claim 5 wherein in the formula (1), $R^4$ is lower alkyl, $R^5$ is lower alkyl, oxoalkyl, or phenyl having 1 to 3 substituents selected from the group consisting of lower alkyl and halogen, or $R^4$ and $R^5$, taken together with the sulfur atom to which they are attached, form a 1,4-oxathiane ring.

7. The naphthyridine compound according to claim 6 wherein in the formula (1), $R^4$ and $R^5$ each represent lower alkyl.

8. The naphthyridine compound according to claim 7, wherein the compound represented by the formula (1) is 1-benzyl-3-(methyl-n-propylsulfonium)-1,8-naphthyridin-2 (1H)-on-4-olate, 1-benzyl-7-methyl- 3-(methyl-n-propylsulfonium)-1,8-naphthyridin-2(1H)-on-4-olate or 1-(3,4,5-trimethoxybenzyl)-3-(methyl-n-propylsulfonium)-1,8-naphthyridin-2(1H)-on-4-olate.

9. The naphthyridine compound according to claim 7, wherein the compound represented by the formula (1) is 1-benzyl-3-(methyl-n-propylsulfonium)-1,8-naphthyridin-2 (1H)-on-4-olate or 1-(3,4,5-trimethoxybenzyl)-3-(methyl-n-propylsulfonium)-1,8-naphthyridin-2(1H)-on-4-olate.

10. The naphthyridine compound according to claim 1 or 2, wherein in the formula (1), A is methylene.

11. The naphthyridine compound according to claim 10, wherein in the formula (1), $R^1$ is an electron pair "-".

12. The naphthyridine compound according to claim 11, wherein in the formula (1), $R^2$ is pyridyl, or is phenyl optionally having 1 to 3 substituents selected from the group consisting of halogen, lower alkyl and lower alkoxy.

13. The naphthyridine compound according to claim 12, wherein in the formula (1), $R^4$ is lower alkyl, $R^5$ is lower alkyl, oxoalkyl, lower alkanoyloxy-lower alkyl, benzoyloxy-lower alkyl having 3 lower alkoxy groups as substituents on the benzene ring or phenyl having one substituent selected from lower alkyl or halogen, or $R^4$ and $R^5$, taken together with the sulfur atom to which they are attached, form a 1,4-oxathiane ring.

14. The naphthyridine compound according to claim 13 wherein in the formula (1), $R^2$ is phenyl optionally having one halogen atom or 1 to 3 lower alkoxy groups as the substituents and $R^4$ and $R^5$ each represent lower alkyl.

15. The naphthyridine compound according to claim 14, wherein the compound represented by the formula (1) is 1-(3,4,5-trimethoxybenzyl)-3-(methyl-n-propylsulfonium)-1,8-naphthyridin-2(1H)-on-4-olate.

16. A pharmaceutical composition comprising the naphthyridine compound of claim 1 as an active ingredient and a pharmaceutically acceptable carrier.

17. An analgesic composition comprising the naphthyridine compound of claim 1 and a pharmaceutically acceptable carrier.

18. A method for relieving a pain in a patient in need of such pain relief, which comprises administering to the patient an effective amount of the naphthyridine compound of claim 1.

* * * * *